United States Patent [19]

Prashad et al.

[11] Patent Number: 5,412,137
[45] Date of Patent: May 2, 1995

[54] PROCESS FOR PREPARING PHOSPHINYLOXY PROPANAMINIUM INNER SALT DERIVATIVES

[75] Inventors: Mahavir Prashad, Hopatcong; Prasad K. Kapa, Parsippany, both of N.J.

[73] Assignee: Sandoz Ltd., Basel, Switzerland

[21] Appl. No.: 197,050

[22] Filed: Feb. 16, 1994

Related U.S. Application Data

[63] Continuation of Ser. No. 73,407, Jun. 7, 1993, abandoned.

[51] Int. Cl.⁶ .................. C07F 9/09; C07F 9/165
[52] U.S. Cl. .................. 558/146; 558/169; 558/170
[58] Field of Search .................. 558/146, 169, 170

[56] References Cited

PUBLICATIONS

Hintze, V. et al. Lipids 10(1), 20–24 (1975); Chem. Abstr. 82(21), 134462 (1975).

Primary Examiner—Mary C. Lee
Assistant Examiner—Michael G. Ambrose
Attorney, Agent, or Firm—Robert S. Honor; Melvyn M. Kessenoff; Thomas O. McGovern

[57] ABSTRACT

A process for preparing compounds of the formula

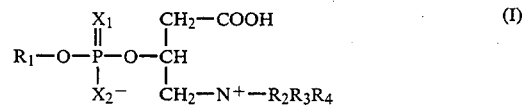

where
$X_1$ and $X_2$ are independently O or S, and
$R_1$ is as defined herein,
$R_2$, $R_3$, and $R_4$ are each independently straight or branched chain $(C_{1-4})$alkyl, and pharmaceutically acceptable salts, physiological hydrolyzable esters, and pro-drug forms thereof, which are useful as hypoglycemic agents.

8 Claims, No Drawings

PROCESS FOR PREPARING PHOSPHINYLOXY PROPANAMINIUM INNER SALT DERIVATIVES

This is a continuation of application Ser. No. 08/073,407, filed Jun. 7, 1993, now abandoned.

The present invention relates to a process for preparing long chain alkyloxy and aryloxy substituted phosphinyloxy derivatives of carnitine. In particlular, it relates to a process for preparing long chain alkoxy and aryloxy substituted 3-carboxyalkyl phosphinyloxy propanaminium, hydroxide, inner salt derivatives and analogs, their preparation, and their use as anti-diabetic agents.

The compounds of the invention may be represented by the following formula:

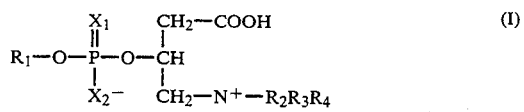

where
X$_1$ and X$_2$ are independently O or S, and
R$_1$ is R$_5$—Y—R$_6$ or R$_7$—Z—R$_8$,
where
Y is —O—, —S—, —CH$_2$—, —CH=CH—, —C≡C—, —N(R$_{10}$)—CO—, or —CO—N(R$_{10}$)—,
Z is —O—, —S— or —CH$_2$—,
R$_5$ is straight or branched chain (C$_{1-17}$)alkyl, or ω-triflouro-(C$_{1-8}$)alkyl, and
R$_6$ is straight chained (C$_{2-18}$)alkylene,
and the total number of carbons in R$_5$—Y—R$_6$ is from 7 to 19,
R$_7$ is unsubstituted phenyl, phenoxyphenyl, biphenyl, naphthyl or naphthoxyphenyl, or phenyl, phenoxyphenyl, biphenyl, naphthyl or naphthoxyphenyl mono-, di-, or tri-substituted with halogen, NO$_2$, NH$_2$, CN, (C$_{1-8}$)alkyl, (C$_{1-8}$)alkoxy, triflouromethyl, triflouromethoxy, or acetyl,
R$_8$ is straight chained (C$_{3-15}$)alkylene, —(CH$_2$)$_m$—N(R$_{10}$)—CO—(CH$_2$)$_n$—, —(CH$_2$)$_m$—CO—N(R$_{10}$)—(CH$_2$)$_n$—, or —CH$_2$—R$_{11}$—O—R$_{12}$—,
m is 1 to 7,
n is 1 to 7,
R$_{10}$ is hydrogen, methyl, or ethyl,
R$_{11}$ is straight or branched chain alkyl of 1 to 7 carbon atoms,
R$_{12}$ is straight chained (C$_{2-7}$)alkylene,
and the total number of carbons in the aryl substituents of R$_7$ and the carbon atoms in R$_8$ is from 3 to 15,
R$_2$, R$_3$, and R$_4$ are each independently straight or branched chain (C$_{1-4}$)alkyl,
and pharmaceutically acceptable salts, physiological hydrolysable esters, and pro-drug forms thereof.

The compounds of Formula (I) in which X$_1$ and X$_2$ are oxygen may be prepared in accordance with the following reaction scheme:

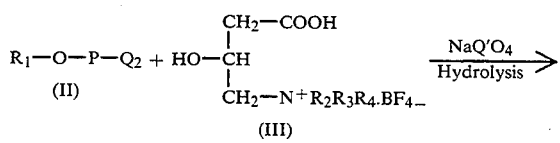

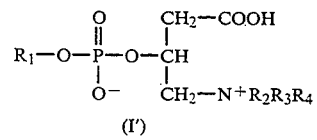

where
Q and Q' are independently chlorine, bromine, or iodine, and
R$_1$, R$_2$, R$_3$, and R$_4$ are as defined above.

The compounds of formula (I') are prepared by reacting a compound of formula (II) with a compound of the formula (III) in an inert solvent, preferably in the presence of a base, and then oxidizing and hydrolysing the product with an alkali metal perhalate, such as sodium periodate. The inert solvent is preferably acetonitrile and the preferred base is collidine. The perhalate is preferably added in water as the hydrolysing agent. The temperature at which the reaction is run is not critical, but temperatures between about 20° C. to about 30° C., especially room temperature, are preferred. The time of the reaction is also not critical, but it is preferred that the reaction of the compounds of formula (II) and (III) be run for about 15 to 20 hours and that the oxidation reaction be run for about 1 to 4 hours. The compound of formula (I) is isolated by conventional techniques, for example, by chromatography.

The compounds of Formula (I) in which X$_1$ and X$_2$ are oxygen may alternatively be prepared by a combination process in accordance with the following reaction scheme

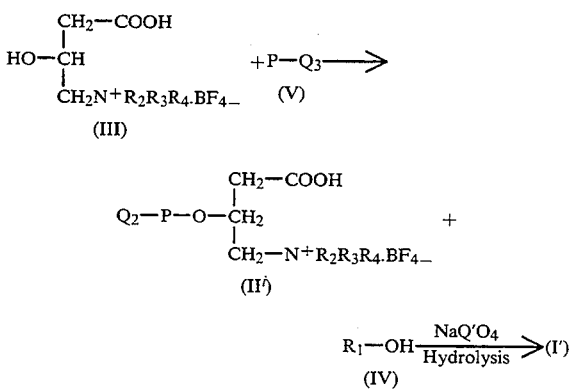

where R$_1$, R$_2$, R$_3$, R$_4$, Q, and Q' are as defined above.

In accordance with the combined process, the compounds of formula (I') are prepared by reacting a compound of formula (III) with a compound of the formula (V) in an inert solvent, then adding the compound of formula (IV) in an inert solvent, and oxidizing and hydrolysing the product obtained with an alkali metal perhalate, such as sodium periodate. The inert solvent used in preparing compound (II$^i$) is preferably acetonitrile and the preferred inert solvent for compound (IV) is tetrahydrofuran. Collidine is the preferred base, and the perhalate used in preparing compound (I') is preferably added in water as the hydrolysing agent. Temperatures at which the reaction is run are not critical; but a temperature of about −40° C. to 0° C. is preferred for reacting compound (III) with compound (V); −0° C. for the reaction with compound (IV); and room temperature for the oxidation reaction. The time of the reaction is also not critical, but it is preferred that the reaction of the compounds of formula (III) and (V) be run for about 2 to 3 hours; the reaction with compound (IV) for about 2 to 4 hours; and the oxidation reaction for about 5 to 20 hours. The compounds of formula (I') are isolated by conventional techniques, for example, by chromatography.

The compounds of Formula (I') may also be prepared in accordance with the following reaction scheme:

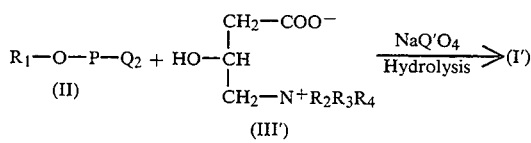

where $R_1$, $R_2$, $R_3$, $R_4$, Q, and Q' are as defined above.

The compounds of formula (I') are prepared by reacting a compound of formula (II) with L-carnitine of formula (III') in an inert solvent preferably in the presence of a base and then oxidizing and hydrolysing the product with an alkali metal perhalate, such as sodium periodate. The inert solvent is preferably tetrahydrofuran, and the perhalate is added in water as the hydrolysing agent. Collidine is the preferred base. The temperature at which the reaction is run is not critical, but temperatures between about 20° C. to about 30° C., especially room temperature, are preferred. It is also preferred that the alkali metal perhalate be added at reaction temperatures maintained between 0° to 15° C. The time of the reaction is also not critical, but it is preferred that the reaction of the compounds of formula (II) and (III') be run for about 3 to 5 hours and that the oxidation reaction be run for about 1 to 4 hours. The compound of formula (I') is isolated and purified by chromatography over reverse phase silica gel (C-8) or AMBERLITE XAD-4 nonionic polymeric adsorbent.

The compounds of formula (I) in which $X_1$ or $X_2$ is sulfur may be prepared by thiolating the product of the reaction of the compound of formula (II) and formula (III) or (III') with sulfur in place of an alkali metal perhalate. The compounds of formula (I) in which $X_1$ and $X_2$ are both sulfur may be prepared by treating the product of the reaction of the compound of formula (II) and formula (III) or (III') with sulfur and hydrogen sulfide instead of the alkali metal perhalate and hydrolysing agent.

The compounds of formula (I) in which a phenyl or naphthyl ring in substituent $R_7$ is mono-, di-, or tri-substituted with an $NH_2$ group may preferably be prepared by reducing the corresponding mono-, di-, or tri-substituted $NO_2$ compound in a standard manner, for example, by hydrogenating the $NO_2$ substituted compound with hydrogen gas over palladium in an inert solvent, and isolating by conventional techniques.

The compound of formula (II) may be prepared in accordance with the following reaction scheme:

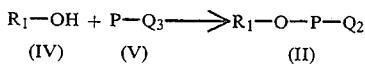

where $R_1$ and Q are as defined above. The compounds of formula (II) are prepared by reacting a compound of formula (IV) with a compound of the formula (V) in an inert anhydrous solvent under an inert atmosphere. The inert solvent is preferably an anhydrous ether, such as diethyl ether, or an anhydrous aromatic solvent, such as toluene. The temperature at which the reaction is run is not critical, but temperatures between about 20° C. to about 30° C., especially room temperature, are preferred. The time of the reaction is also not critical, but it is preferred that the reaction be run for about 2 to 3 hours. The compound of formula (II) is isolated by conventional techniques, for example, by distillation.

The aliphatic alcohols of formula (IV) in which $R_1$ is $R_5$—Y—$R_6$ and Y is oxygen or sulfur may be prepared in accordance with the following reaction scheme:

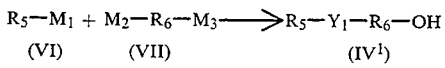

where
$M_1$ is —OH, —SH or Q
$M_2$ is —OH or Q,
$M_3$ is —OH or protected —OH,
$Y_1$ is —O— or —S—, and
$R_5$ and $R_6$ are as defined above, provided at least one of $M_1$ or $M_2$ is halo and the other is —OH or —SH.

The compounds of formula (IV$^i$) are prepared by reacting a compound of formula (VI) with a compound of the formula (VII) in an inert solvent in the presence of an alkali metal hydride and deprotecting the compound of formula (IV$^i$) when $M_3$ is protected —OH. Dimethylformamide is the preferred solvent and sodium hydride is the preferred alkali metal hydride. When $M_3$ is a protected hydroxy group, the protecting group can be any conventional hydroxy protecting group, such as dihydropyran. The temperature at which the reaction is run is not critical, but temperatures between about 20° C. to about 30° C., especially room temperature, are preferred. The time of the reaction is also not critical, but it is preferred that the reaction be run for about 10 to 48 hours. If $M_3$ is dihydrofuran protected—OH, the protecting group can be removed by treating the compound with an acid, such as p-toluenesulfonic acid. The compound of formula (IV$^i$) is isolated by conventional techniques, for example, by chromatography or extraction.

Alternatively, the alcohols of formula (IV) in which $R_1$ is $R_5$—O—$R_6$ may be prepared in accordance with the following reaction scheme:

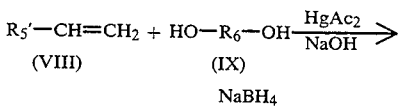
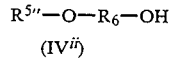

where
$R_5'$ is ($C_{1-15}$)alkyl,
$R_5''$ is ($C_{3-17}$)alkyl, and
$R_6$ is as defined above.

The compounds of formula (IV$^{ii}$) are prepared by reacting a compound of formula (VIII) with a compound of the formula (IX) in an inert solvent in the presence of mercuric acetate and then treating the reactants with aqueous sodium hydroxide and sodium borohydride. Dimethylformamide is the preferred inert solvent. The temperature at which the reaction is run is not critical, but temperatures between about 20° C. to about 30° C., especially room temperature, are preferred. The time of the reaction is also not critical, but it is preferred that the reaction be run for about 10 to 20 minutes. The compound of formula (IV$^{ii}$) is isolated by conventional techniques, for example, by chromatography.

The amido alcohols of formula (IV) in which R$_1$ is R$_5$—Y—R$_6$ and Y is —N(R$_{10}$)—CO— may be prepared in accordance with the following reaction scheme:

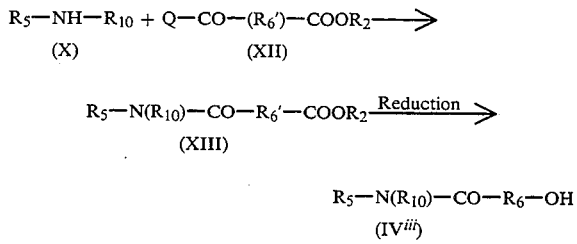

where

Q, R$_2$, R$_5$, R$_6$, and R$_{10}$ are as defined above and R$_6'$ is (C$_{1-17}$)alkylene.

The compounds of formula (IV$^v$) are prepared by reacting a compound of formula (X) with a compound of the formula (XII) in an inert solvent, for example methylene chloride, in the presence of a base, such as triethylamine. The intermediate of formula (XIII) obtained is isolated and then reduced preferably in an inert solvent, for example, tertiary butyl alcohol and methanol, with sodium borohydride. It is preferred that the reaction between compounds (X) and (XII) be carried out at room temperature over a period of about 15 to 20 hours and that the reduction of compound (XIII) be run at reflux temperature for about 12 to 24 hours. The compounds of formula (XIII) and (IV$^{iii}$) can be isolated by conventional techniques, for example, by extraction and chromatography.

The amido alcohols of formula (IV) in which R$_1$ is R$_7$—Z—R$_8$ and R$_8$ is —(CH$_2$)$_m$—N(R$_{10}$)—CO—(CH$_2$)$_n$— may be prepared similarly in accordance with the following reaction scheme:

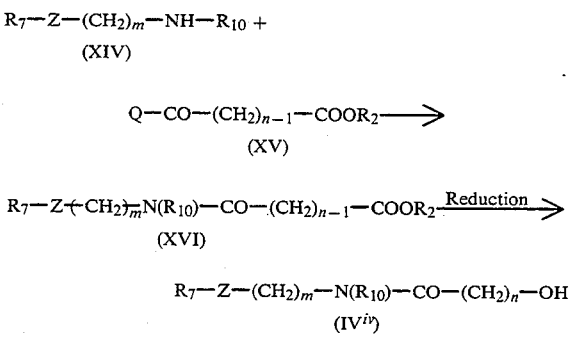

where m, n, Q, Z, R$_2$, R$_7$, R$_8$, and R$_{10}$ are as defined above.

The compounds of formula (IV$^{iv}$) are prepared by reacting a compound of formula (XIV) with a compound of the formula (XV) and reducing with sodium borohydride in the same manner as in the preparation of the compound of formula (IV$^{iii}$) above.

The amido alcohols of formula (IV) in which R$_1$ is R$_5$—Y—R$_6$ and Y is —CO—N(R$_{10}$)— may be prepared in accordance with the following reaction scheme:

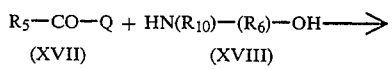

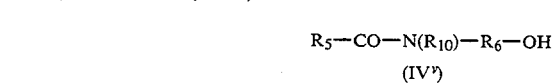

where Q, R$_2$, R$_5$, R$_6$, and R$_{10}$ are as defined above.

The compounds of formula (IV$^v$) are prepared by standard procedures, for example, by adding a compound of formula (XVII) to a compound of the formula (XVIII) in an inert solvent, such as methylene chloride, in the presence of a base, such as triethylamine at about 0° C. and then allowing the reaction to proceed at room temperature over a period of about 12 to 24 hours. The compounds of formula (IV$^v$) can be isolated by conventional techniques, for example, by extraction and chromatography.

The amido alcohols of formula (IV) in which R$_1$ is R$_7$—Z—R$_8$ and R$_8$ is —(CH$_2$)$_m$—CO—N(R$_{10}$)—(CH$_2$)$_n$— may be prepared similarly in accordance with the following reaction scheme:

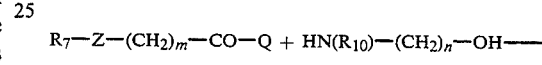

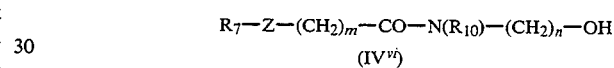

where m, n, Q, Z, R$_7$, and R$_{10}$ are as defined above.

The compounds of formula (IV$^{vi}$) are prepared by reacting a compound of formula (XIX) with a compound of the formula (XX) in the same manner as in the preparation of the compound of formula (IV$^v$) above.

The aromatic alcohols of formula (IV) in which R$_1$ is R$_7$—Z—R$_8$ and Z is oxygen or sulfur may also be prepared in accordance with the following reaction scheme:

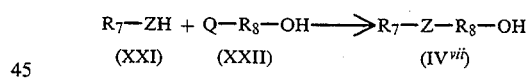

where Q, Z, R$_7$, and R$_8$ are as defined above.

The compounds of formula (IV$^{vii}$) are prepared by reacting a compound of formula (XXI) with a compound of the formula (XXII) in an inert solvent in the presence of an alkali metal hydride using the same reaction conditions as in the preparation of the compounds of formula (IV$^i$) above. The compound of formula (IV$^{iv}$) is isolated by conventional techniques, for example, by chromatography or extraction.

Alternatively, the alcohols of formula (IV$^{vii}$) may be prepared in accordance with the following reaction scheme:

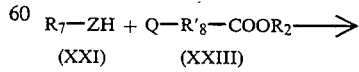

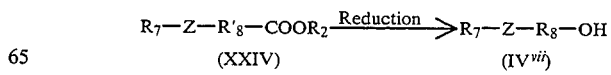

where

Q, Z, R$_2$, and R$_7$ are as defined above, and

R'8 is straight chained $(C_{3-14})$alkylene, $-(CH_2)_m-N(R_{10})-CO-(CH_2)_{n-1}-$, $-(CH_2)_m-CO-N(R_{10})-(CH_2)_{n-1}-$, or $-CH_2R_{11}-O-R_{12}-$, m, n, $R_{10}$, $R_{11}$, are as defined above, and $R_{12}$ is $(C_{2-6})$ alkylene.

The compounds of formula (IV$^{vii}$) are prepared by reacting a compound of formula (XXI) with an ester of the formula (XXIII) in an inert solvent in the presence of an alkali metal hydride or alkali metal carbonate and then reducing the intermediate of formula (XXIV) with a reducing agent, such as lithium aluminum hydride, to obtain an alcohol of formula (IV$^{iv}$). Compounds of formula (XXIV) are prepared using the same reaction conditions as in the preparation of the compounds of formula (IV') above, when an alkali metal hydride is used, and for longer reaction times up to four days, when an alkali metal carbonate is used. The compound of formula (XXIV) can be reduced in situ or isolated first by conventional techniques, for example, chromatography. Reduction of the compounds of formula (XIII) is carried out in an inert anhydrous solvent, such as diethyl ether, preferably at reflux temperature over a period of from about 30 minutes to about 3 hours and optionally at room temperature for up to 4 days. The compound of formula (IV$^{vii}$) is isolated by conventional techniques, for example, by extraction.

The Compounds of formula (XXI) in which $R_7$ is phenyl or naphthyl substituted by alkoxy of 1 to 8 carbon atoms may be prepared in accordance with the following reaction scheme:

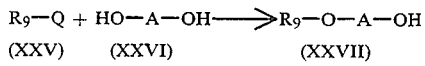

$$R_9-Q + HO-A-OH \longrightarrow R_9-O-A-OH$$
$$(XXV) \qquad (XXVI) \qquad\qquad (XXVII)$$

where

A is phenyl or naphthyl and $R_9$ is $(C_{1-8})$alkyl.

The compounds of formula (XXVII) are prepared by reacting a compound of formula (XXV) with a compound of the formula (XXVI) in an inert solvent in the presence of a halogen scavenging agent, such as potassium carbonate. Dimethylformamide is the preferred inert solvent. It is also preferred that the reaction be run at temperatures between about 50° C. to about 80° C. for about 15 to 20 hours. The compound of formula (XXVII) is isolated by conventional techniques, for example, by chromatography.

The compounds of formula (II) in which $R_7$ is unsubstituted or substituted phenyl or naphthyl substituted by unsubstituted or substituted phenoxy or naphthoxy may be prepared in accordance with the following reaction scheme:

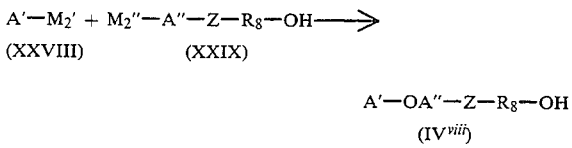

$$A'-M_2' + M_2''-A''-Z-R_8-OH \longrightarrow$$
$$(XXVIII) \qquad (XXIX)$$

$$A'-OA''-Z-R_8-OH$$
$$(IV^{viii})$$

where

A' and A'' are each independently phenyl or naphthyl unsubstituted or substituted with halogen, $NO_2$, $NH_2$, CN, $(C_{1-8})$alkyl, $(C_{1-8})$alkoxy, ω-triflouro-$(C_{1-8})$alkyl, triflouromethoxy, or acetyl, one of $M_2'$ or $M_2''$ is OH and the other is bromo, and $R_8$ is as defined above.

The compounds of formula (IV$^{viii}$) are prepared by reacting a compound of formula (XXVIII) with a compound of the formula (XXIX) preferably in an inert soflvent such as pyridine, and in the presence of potassium carbonate and copper oxide. It is also preferred that the reaction be run at temperatures between about 50° C. to about reflux for about one to two days. The compound of formula (IV$^{viii}$) is isolated by conventional techniques, for example, by flash chromatography.

The alcohols of formula (XXIX) may be prepared in accordance with the following reaction scheme:

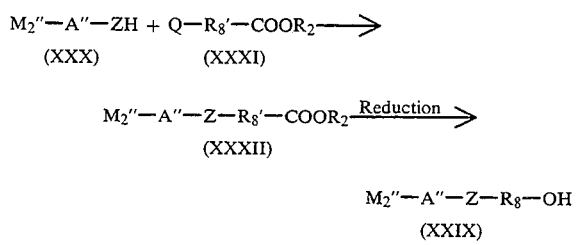

$$M_2''-A''-ZH + Q-R_8'-COOR_2 \longrightarrow$$
$$(XXX) \qquad\qquad (XXXI)$$

$$M_2''-A''-Z-R_8'-COOR_2 \xrightarrow{\text{Reduction}}$$
$$(XXXII)$$

$$M_2''-A''-Z-R_8-OH$$
$$(XXIX)$$

where $M_2''$, A'', Z, $R_3$, $R_8$ and $R_8'$ are as defined above.

The compounds of formula (XXIX) are prepared by reacting a compound of formula (XXX) with an ester of the formula (XXXI) in an inert solvent, such as dimethylformamide, in the presence of an alkali metal carbonate and then reducing the intermediate of formula (XXXII) with a reducing agent, such as lithium aluminum hydride or DIBAL-H. Preferably, the reaction of the compound of formula (XXX) with the ester of the formula (XXXI) is carried out at a temperature between room temperature and reflux temperature over a period of up to 4 days. The compound of formula (XXXII) can be reduced in situ or isolated first by conventional techniques, for example, chromatography. Reduction of the compounds of formula (XIII) is carried out in an inert anhydrous solvent, such as diethyl ether or tetrahydrofuran, preferably under an inert atmosphere between room temperature and reflux temperature over a period of from about 1 to about 6 hours. The compound of formula (XXIX) is isolated by conventional techniques, for example, by extraction.

Pharmaceutically acceptable metal salts, such as the sodium or potassium salt can be formed using conventional methods. In addition, acid addition salts, such as the hydrochloride, can be formed by reacting the compounds of formula (I) with an appropriate acid.

The pharmaceutically acceptable esters of this invention include not only the esters formed with the carboxylic acid group of the carnitine moieity but also orthoesters formed with the phosphate moieity. Carboxylic esters can be prepared by reacting a compound of formula (II) with the desired ester form of the carnitine of formula (III). The phosphate esters of formula (I) may be prepared by reacting the product of the reaction of the compound of formula (II) and formula (III) with the desired alcohol before treating the product with an alkali metal perhalate. The instant invention also includes pro-drug forms of the compounds of formula (I). Such pro-drugs are known and described in the literature, for example in PCT application WO91/19721. These esters and pro-drugs include the pivaloyloxymethyl, 4-(2-methoxyphenoxy)-2-methylbutyryloxymethyl, N,N-dimethoxyethylcarbamoylmethyl, N-

(3,6,9-trioxadecyl)-N-methylcarbamoylmethyl, N-(3,6,-dioxaheptyl)-N-methylcarbamoylmethyl, N,N-dipentylcarbamoylmethyl, N,N-dipropylcarbamoylmethyl, N,N-dibutylcarbamoylmethyl, and N-(2-methoxyphenoxyethyl)-N-methylcarbamoylmethyl esters of carnitine.

The compounds of formula (I) may exist in the form of optically active isomers and can be separated and recovered by conventional techniques. The L-carnitine forms of the compounds of formula (I) are preferred. Compounds in which one of $X_1$ or $X_2$ is a sulfur atom exist in tautomeric form and can exist in the form of diastereoisomers, which can also be separated and recovered by conventional techniques. Similarly, compounds of the invention containing a double bond can exist in the form of geometric isomers, which can be readily separated and recovered by conventional procedures. Such isomeric forms are included in the scope of this invention.

Many of the compounds of formulas (III) to (XXVI) are known and may be prepared by methods described in the literature. The starting materials not specifically disclosed in the art may be prepared by analogous methods or as described in the examples below using known starting materials.

As indicated above, the compounds of formula (I) exhibit pharmacological activity in animals. In particular, the compounds of formula (I) are hypoglycemic agents and are useful in the treatment of diabetes, as indicated by the acute and chronic hypoglycemic screen tests in male Sprague-Dawley rats, given 1 to 100 mg/kg of drug. The rats, approximately 2 to 3 months of age, weighing about 250 grams in the acute screen test and about 200 to 220 grams in the chronic screen test, are kept in a room at a controlled ambient temperature of 72° F. and a 12/12 hour light/dark cycle for at least seven days before the acute screen test and seven days before and during testing in the chronic screen test.

In the acute screen test, Purina rat chow and water are available ad libitum. Following an 18 hour fast, rats (5/group) are given test compounds orally by gavage in 0.5% carboxymethylcellulose with 0.2% Tween 80. The animals receive 1.0 ml/100 g body wt. Three hours after administration, the rats are anesthetized with $CO_2$ and blood collected via cardiac puncture. Sera are collected and used for glucose and $\beta$-hydroxybutyrate determination. Glucose is measured by the glucose oxidase method (YSI Model 27 or 2700, Yellow Springs, Ohio) and $\beta$-hydroxybutyrate is assayed with a $\beta$-hydroxybutyrate dehydrogenase-linked enzyme assay (Sigma Kit 310-uv; St. Louis, Mo.). The ED50 value is the amount of compound required to produce a 50% of maximum reduction in $\beta$-hydroxybutyrate.

In the chronic screen test, the rats are fed a high fat diet ad libitum. At fed state, 37.5 to 40 mg of streptozotocin/kg of body weight are injected via the tail vein. Five days later, those rats are considered to be diabetic which have fed blood glucose of greater than 200 mg/dl and, following an overnight fast, when given an oral glucose tolerance test, have blood glucose of 40 to 80 mg/dl three hours after the test. Four days later, animals are used in the screen, if fed blood glucose levels are greater than 180 mg/dl. Blood glucose is determined with a YSI Glucose Analyzer. The chronic screen test is carried out as follows:

On Day 1, food is removed from rats at 8:00 A.M.; and after an initial blood glucose reading is taken via the tip of the tail, vehicle (control) or compound in vehicle (9 rats/treatment) is administered orally. Six hours later blood glucose level is measured; and immediately thereafter the rats are refed. The same rats are given either vehicle or drug once a day for 11 consecutive days. Blood glucose is determined at 0 hour and after a 6-hour fast post-dosing on days 4, 8, and 11. The ED50 value, calculated on day 11, is the amount of compound required to produce 50% of maximal efficacy in ability of the compound to normalize blood glucose levels. Efficacy of 100% represents restoration of blood glucose levels to that of a normal rat.

The antidiabetic effective dosage of the compounds of formula (I) employed for the alleviation of the above condition will vary depending on the particular compound employed, the mode of administration and severity of the condition being treated. However, in general, satisfactory results are obtained when the compounds of formula (I) are administered at a daily dosage of from about 1 milligram to about 100 milligrams per kilogram of animal body weight, optionally given in divided doses two to four times a day, or in sustained release form. For the larger mammals, for example primates such as humans, the total daily dosage is from about 1 to about 1000, preferably about 5 to about 500, milligrams per day. Unit dosage forms comprise from about 1, preferably about 5 to about 250 milligrams of the active compound in intimate admixture with a solid or liquid pharmaceutically acceptable carrier or diluent. The compounds of the invention may be administered in a manner similar to known standards for the above uses. The suitable daily dosage for a particular compound will depend on a number of factors, such as its relative potency of activity. It has been determined that the compound of Example 1, (R)-3-carboxy-N,N,N-trimethyl-2-{[hydroxy(tetradecyloxy)phosphinyl]oxy}-1-propanaminium hydroxide, inner salt has an ED50 of 4.2 mg/kg in the acute hypoglycemia test and 45 mg/kg/day in the chronic hypoglycemia test. Compound 62 of Example 7, (R)-3-Carboxy-N,N,N-trimethyl-2-[[hydroxy{4-[3-(hexyloxy)phenoxy]butyloxy}phosphinyl]oxy]-1-propanaminium hydroxide, inner salt, has an ED50 of 1.6 mg/kg in the acute hypoglycemia test and an $ED_{70}$ of 37 mg/kg/day in the chronic hypoglycemia test. An indicated daily dose for the compounds is from about 1 to about 1000, preferably about 5 to about 500, especially about 20 to about 250 mg p.o. for the larger primates, such as humans.

For the above use, the compounds of formula (I) may be administered orally or parenterally as such or admixed with conventional pharmaceutical carriers. They may be administered orally in such forms as tablets, dispersible powders, granules, capsules, syrups and elixirs, and parenterally as solutions or emulsions. These pharmaceutical preparations may contain up to about 90% of the active ingredient in combination with the carrier or adjuvant.

Capsules containing the ingredients indicated below may be prepared by conventional techniques:

| Ingredient | Weight (mg) |
| --- | --- |
| (R)-3-carboxy-N,N,N-trimethyl-2-{[hydroxy(tetradecyloxy)phosphinyl]oxy}-1-propanaminium hydroxide, inner salt | 25 |
| Microcrystalline cellulose | 65.66 |
| Mannitol | 65.66 |
| Colloidal silicon dioxide | 0.16 |
| Hydrogenated castor oil | 6.52 |

-continued

| Ingredient | Weight (mg) |
|---|---|
| | 163.00 |

EXAMPLE 1

(R)-3-Carboxy-N,N,N-trimethyl-2-{[hydroxy(tetradecyloxy)phosphinyl]oxy}-1-propanaminium Hydroxide, Inner Salt Through a solution of 46.8 ml of $PCl_3$ in 200 ml of anhydrous ether and 93.4 ml of anhydrous toluene, dry nitrogen is bubbled for five minutes. Nitrogen is also bubbled through a solution of 20 gm of tetradecanol in 200 ml of anhydrous ether for five minutes. The alcohol solution is added to the $PCl_3$ solution dropwise with stirring over a period of 20 minutes and then stirred for a further two hours. The solvents are removed via distillation to give dichlorotetradecylphosphite as a clear colourless liquid.

To a solution of 16.4 gm of the tetrafluoroborate salt of L-carnitine and 26 gm of collidine in 263 ml of acetonitrile is added 29.4 gm of dichlorotetradecylphosphite. The reaction mixture is stirred at room temperature for 17 hours and then a solution of 21.1 gm of sodium metaperiodate in 48.7 ml of water is added. After stirring at room temperature for two hours, the reaction mixture is filtered through Celite and the filtrate is concentrated under vacuum. The residue is flash chromatographed on normal phase silica gel, initially with a 50/30/3 ratio of chloroform/methanol/concentrated ammonium hydroxide and then with a 50/30/10 ratio of the same solvent system to yield a product that is then flash chromatographed on LiChroprep RP-8 silica gel using gradients from water to acetonitrile and to methanol. The title compound is isolated as an amorphous solid, (m.p. ~190° C. [dec]; $^{31}P$ NMR=0.324 ppm; $[\alpha]^{25}$=−10.34 C=1.0 MeOH).

Following the above procedure and using an equivalent amount of D-carnitine in place of the L-carnitine, there is obtained the D-carnitine form of the title compound (m.p. ~190° C. [dec.]; $^{31}P$ NMR=0.286 ppm; $[\alpha]^{25}$=+10.92 C=0.97 MeOH).

The N,N-diethylcarboxamidylmethyl ester (m.p. ~60° C. [softening]; $^{31}P$ NMR=0.091 ppm) or pivaloyloxymethyl ester (m.p. ~139° C. [dec.]; $^{31}P$ NMR=0.081 ppm) pro-drug of the title compound may be prepared by reacting the title compound with N,N-diethyl-2-chloroacetamide in ethyl alcohol and triethylamine or chloromethyl pivaloate in dimethylformamide and triethylamine in the presence of sodium iodide.

When an equivalent amount of
1) tridecanol;
2) pentadecanol;
3) cis-7-tetradecenol;
4) cis-11-tetradecenol; or
5) pentadec-7-yne-1-ol
is substituted for the tetradecanol in the above procedure, there is obtained:

1) (R)-3-Carboxy-N,N,N-trimethyl-2-{[hydroxy(tridecyloxy)phosphinyl]oxy}-1-propanaminium, hydroxide, inner salt (m.p. ~190° C. [dec]; $^{31}P$ NMR=0.094 ppm);

2) (R)-3-Carboxy-N,N,N-trimethyl-2-{[hydroxy(pentadecyloxy)phosphinyl]oxy}-1-propanaminium, hydroxide, inner salt (m.p. ~190° C. [dec]; $^{31}P$ NMR=0.098 ppm);

3) (R)-3-Carboxy-N,N,N-trimethyl-2-[[hydroxy{[7-(Z)-tetradecenyl]oxy}phosphinyl]oxy]-1-propanaminium, hydroxide, inner salt ($^{31}P$ NMR=0.078 ppm);

4) (R)-3-Carboxy-N,N,N-trimethyl-2-[[hydroxy{[11-(Z)-tetradecenyl]oxy}phosphinyl]oxy]-1-propanaminium, hydroxide, inner salt ($^{31}P$ NMR=0.115 ppm); or 5) (R)-3-Carboxy-N,N,N-trimethyl-2-{[hydroxy(7-pentadecynyloxy)phosphinyl]oxy}-1-propanaminium, hydroxide, inner salt ($^{31}P$ NMR=0.059 ppm), respectively.

EXAMPLE 2

(R)-2-Carboxymethyl-4-hydroxy-N,N,N-trimethyl-3,5,10-trioxa-4-phosphanonadecan-1-aminium Hydroxide, Inner Salt, 4-oxide Step A. 4-nonyloxybutanol To a solution of 7.1 ml of 1,4-butanediol in 40 ml of dimethylformamide, 1.8 gms of sodium hydride are added; and the reaction mixture is stirred at room temperature for 15 minutes. To this solution is added 7.6 ml of bromononane and the reaction mixture is stirred at room temperature for 44 hours. The reaction mixture is then partitioned between ethyl acetate and water and the organic layer is washed with brine, dried over sodum sulfate, filtered, and concentrated under vacuum. The residue is flash chromatographed with an 8/1 ratio of ethyl acetate and hexane to give 4-nonyloxybutanol as a clear colorless liquid.

When an equivalent amount of:
6) 1,12-dodecanediol and iodomethane;
7) 1,6-hexanediol and bromoheptane;
8) 1,8-octanediol and bromopentane;
9) 1,10-decanediol and bromopropane;
10) 1,2-ethanediol and bromoundecane;
11) 1,9-nonanediol and 1-bromo-3,3-dimethylbutane;
12) 1,5-pentanediol and bromooctane;
13) 1,5-pentanediol and 3-bromodecane; or
14) 1,9-nonanediol and 4,4,4,-triflourobutyl bromide,
are substituted for the 1,4 butanediol and nonanol in the above procedure, the following alcohols are produced:
6) 12-methyloxydodecanol;
7) 6-heptyloxyhexanol;
8) 8-pentyloxyoctanol;
9) 10-propyloxydecanol;
10) 2-undecyloxyethanol;
11) 9-(3,3-dimethylbutyloxy)nonanol;
12) 5-octyloxypentanol;
13) 5-(3-decyloxy)-pentanol;
14) 9-(4,4,4-triflourobutyloxy)nonanol, respectively.

Step B. (R)-2-Carboxymethyl-4-hydroxy-N,N,N-trimethyl-3,5,10-trioxa-4-phosphanonadecan-1-aminium Hydroxide, Innersalt, 4-oxide When the procedure of example 1 is carried out using an equivalent amount of the 4-nonyloxybutanol of step A of this example in place of the tetradecanol, there is obtained (R)-2-Carboxymethyl-4-hydroxy-N,N,N-trimethyl-3,5,10-trioxa-4-phosphanonadecan-1-aminium hydroxide, inner salt, 4-oxide (m.p. ~190° C. [dec]; $^{31}P$ NMR=0.050 ppm).

Following the procedure of example 1 and using an equivalent amount of the alcohols 6 through 14 of step A of this example in place of the tetradecanol, there is obtained:

6) (R)-2-Carboxymethyl-4-hydroxy-N,N,N-trimethyl-3,5,18-trioxa-4-phosphanonadecan-1-aminium hydroxide, inner salt, 4-oxide (m.p. ~190° C. [dec]; $^{31}$P NMR=0.077 ppm);

7) (R)-2-Carboxymethyl-4-hydroxy-N,N,N-trimethyl-3,5,12-trioxa-4-phosphanonadecan-1-aminium hydroxide, inner salt, 4-oxide (m.p. ~190° C. [dec]; $^{31}$P NMR=0.074 ppm);

8) (R)-2-Carboxymethyl-4-hydroxy-N,N,N-trimethyl-3,5,14-trioxa-4-phosphanonadecan-1-aminium hydroxide, inner salt, 4-oxide (m.p. ~190° C. [dec]; $^{31}$P NMR=0.105 ppm);

9) (R)-2-Carboxymethyl-4-hydroxy-N,N,N-trimethyl-3,5,16-trioxa-4-phosphanonadecan-1-aminium hydroxide, inner salt, 4-oxide (m.p. ~190° C [dec]; $^{31}$P NMR=0.064 ppm);

10) (R)-2-Carboxymethyl-4-hydroxy-N,N,N-trimethyl-3,5,8-trioxa-4-phosphanonadecan-1-aminium hydroxide, inner salt, 4-oxide (m.p. ~190° C. [dec]; $^{31}$P NMR=0.002 ppm);

11) (R)-2-Carboxymethyl-4-hydroxy-N,N,N,18,18-pentamethyl-3,5,15-trioxa-4-phosphanonadecan-1-aminium hydroxide, inner salt, 4-oxide (m.p. ~195° C. [dec]; $^{31}$P NMR=0.066 ppm);

12) (R)-2-Carboxymethyl-4-hydroxy-N,N,N-trimethy-3,5,11-trioxa-4-phosphanonadecan-1-aminium hydroxide, inner salt, 4-oxide (m.p. ~197° C. [dec]; $^{31}$P NMR=0.294 ppm);

13) (R)-2-Carboxymethyl-4-hydroxy-12-ethyl-N,N,N-trimethyl-3,5,11-trioxa-4-phosphanonadecan-1-aminium hydroxide, inner salt, 4-oxide (m.p. ~185° C. [dec]; $^{31}$P NMR=0.040 ppm); or 14) (R)-2-Carboxymethyl-4-hydroxy-N,N,N-trimethyl-19,19,19-triflouro-3,5,15-trioxa-4-phosphanonadecan-1-aminium hydroxide, inner salt, 4-oxide (m.p. ~185° C. [dec]; $^{31}$P NMR=0.052); respectively.

EXAMPLE 3

(R)-2-Carboxymethyl-4-hydroxy-N,N,N,12-tetramethyl-3,5,11-trioxa-4-phosphanonadecan-1-aminium Hydroxide, Inner Salt Step A. 5-(2-nonyloxy)pentanol To a mixture of 12.6 grams of mercuric acetate and 8.3 grams of 1,5-pentanediol in 100 ml of dimethylformamide is added 5.0 grams of 1-nonene. The mixture is stirred at room temperature for ten minutes and 40 ml of an aqueous NaOH solution (3 Molar) is added followed by 40 ml of an aqueous NaBH$_4$ solution (0.5 Molar in 3 Molar NaOH). The solution is decanted from the mercuric salts and concentrated. The residue is partitioned between ethyl acetate and water and the organic layer is washed with brine, dried over sodium sulfate, filtered, and concentrated under vacuum to give a clear liquid. This liquid is flash chromatographed, initially with a 19 to 1 ratio of hexane to ethyl acetate and, subsequently, with a 9 to 1 ratio, to give 5-(2-nonyloxy)pentanol as a clear liquid.

When an equivalent amount of:
15) 1,6-hexanediol and 1-octene;
16) 1,4-butanediol and 1-decene;
17) 1,8-octanediol and 2-methylhex-1-ene;
18) 1,9-nonanediol and 2-methylpent-1-ene;
19) 1,7-heptanediol and 2-methylhept-1-ene; or
20) 1,5-pentanediol and 2-methylnon-1-ene;
are substituted for the 1,5-pentanediol and the 1-nonene in the above procedure, the following alcohols are obtained:
15) 6-(2-octyloxy)hexanol;
16) 4-(2-decyloxy)butanol;
17) 8-[2-(2-methyl)hexyloxy]octanol;
18) 9-[2-(2-methyl)pentyloxy]nonanol;
19) 7-[2-(2-methyl)heptyloxy]heptanol; or
20) 5-[2-(2 methyl)nonyloxy]pentanol, respectively.

Step B. (R)-2-Carboxymethyl-4-hydroxy-N,N,N,12-tetramethyl-3,5,11-trioxa-4-phosphanonadecan-1-aminium hydroxide, Inner Salt, 4-oxide When the procedure of example 1 is carried out using an equivalent amount of the 5-(2-nonyloxy)pentanol of step A of this example in place of the tetradecanol, there is obtained (R)-2-carboxymethyl-4-hydroxy-N,N,N,12-tetramethyl-3,5,11-trioxa-4-phosphanonadecan-1-aminium hydroxide, inner salt, 4-oxide (m.p. ~195° C. [dec]; $^{31}$P NMR=0.001 ppm).

Following the procedure of example 1 and using an equivalent amount of the alcohols 15 through 20 of step A of this example in place of the tetradecanol, there is obtained:

15) (R)-2-Carboxymethyl-4-hydroxy-N,N,N,13-tetramethyl-3,5,12-trioxa-4-phosphanonadecan-1-aminium hydroxide, inner salt, 4-oxide (m.p. ~197° C. [dec]; $^{31}$P NMR=0.288 ppm);

16) (R)-2-Carboxymethyl-4-hydroxy-N,N,N,11-tetramethyl-3,5,10-trioxa-4-phosphanonadecan-1-aminium hydroxide, inner salt, 4-oxide (m.p. ~197° C. [dec]; $^{31}$P NMR=0.012 ppm);

17) (R)-2-Carboxymethyl-4-hydroxy-N,N,N,15,15-pentamethyl-3,5,14-trioxa-4-phosphanonadecan-1-aminium hydroxide, inner salt, 4-oxide (m.p. ~185° C. [dec]; $^{31}$P NMR=0.240 ppm);

18) (R)-2-Carboxymethyl-4-hydroxy-N,N,N,16,16-pentamethyl-3,5,15-trioxa-4-phosphanonadecan-1-aminium hydroxide, inner salt, 4-oxide (m.p. ~198° C. [dec]; $^{31}$P NMR=0.238 ppm);

19) (R)-2-Carboxymethyl-4-hydroxy-N,N,N,14,14-pentamethyl-3,5,13-trioxa-4-phosphanonadecan-1-aminium hydroxide, inner salt, 4-oxide (m.p. ~197° C. [dec]; $^{31}$P NMR=0.058 ppm); or 20) (R)-2-Carboxymethyl-4-hydroxy-N,N,N,12,12-pentamethyl-3,5,11-trioxa-4-phosphanonadecan-1-aminium hydroxide, inner salt, 4-oxide (m.p. ~197° C. [dec]; $^{31}$P NMR=0.278 ppm), respectively.

EXAMPLE 4

(R)-2-Carboxymethyl-4-hydroxy-N,N,N,17-tetramethyl 3,5,14-trioxa-4-phosphanonadecan-1-aminium Hydroxide, Inner Salt 4-oxide Step A. 8-(3-methylpentyloxy)octanol To a solution of 5.0 gms of 8-bromo-1-octanol in 25 ml of anhydrous diethyl ether, 22 ml of dihydropyran and 0.050 gms of p-toulenesulfonic acid are added; and the reaction is stirred at room temperature for 16 hours. To this is added 1.0 gms of NaHCO$_3$ and the mixture is stirred for 10 minutes at room temperature, decanted, dried over Na$_2$SO$_4$, filtered, and concentrated to give a clear liquid. This liquid is flash chromatographed with a 98/2 ratio of hexane to ethyl acetate to give the protected bromo-alcohol as a clear liquid.

To a solution of 1.67 gms of 3-methyl pentanol in 40 ml of dimethylformamide, 0.62 gms of sodium hydride are added; and the reaction mixture is stirred at room temperature for 1 hour. To this solution is added 4.0 gms of the protected bromo-alcohol and the reaction mixture is stirred at room temperature for 17 hours. The reaction mixture is then partitioned between ethyl acetate and water. The organic layer is washed with brine, dried over Na$_2$SO$_4$, filtered, and concentrated under vacuum to give a yellow liquid. To a solution of 4.0 gms of this liquid in 240 ml of methanol is added 0.40 gms of p-toluenesulfonic acid and the reaction is stirred at room temperature for 16 hours. The methanol is removed under reduced pressure, and the residue is partitioned between ethyl acetate and water. The organic layer is washed with aqueous NaHCO$_3$ and brine, then dried over Na$_2$SO$_4$, filtered, and concentrated under vacuum to give 8-(3-methylpentyloxy)octanol.

Step B. (R)-2-Carboxymethyl-4-hydroxy-N,N,N,17-tetramethyl-3,5,14-trioxa-4-phosphanonadecan-1-aminium Hydroxide, Inner Salt, 4-oxide When the procedure of example 1 is carried out using an equivalent amount of the 8-(3-methylpentyloxy) octanol of step A of this example in place of the tetradecyl alcohol, there is obtained (R)-2-Carboxymethyl-4-hydroxy-N,N,N,17-tetramethyl-3,5,14-trioxa-4-phosphanonadecan-1-aminium hydroxide, inner salt, 4-oxide (m.p. ~197° C. [dec]; $^{31}$P NMR=0.284 ppm).

EXAMPLE 5

(R)-3-Carboxy-N,N,N-trimethyl-2-[[hydroxy{8-[(4-trifluoromethoxy)phenoxy]octyloxy}phosphinyl]oxy]-1-propanaminium Hydroxide, Inner Salt Step A. 8-(4-(Trifluoromethoxy)phenoxy)-1-octanol A mixture of 5.0 g of 4-(trifluoromethoxy)phenol, 5.87 g of 8-bromo-1-octanol, and 7.76 g of K$_2$CO$_3$ in 56 ml of anhydrous dimethylformamide is stirred and heated at 80° C. for 16 hours. The reaction mixture is poured into dilute HCl solution and the mixture is extracted three times with ethyl acetate. The combined extracts are washed with brine and dried over MgSO$_4$. After filtration and concentration, the crude product is purified by flash chromatography on silica gel, eluting with a 4:1 hexane/ethyl acetate mixture to give the title compound 8-(4-(trifluoromethoxy)-phenoxy)-1-octanol.

When an equivalent amount of:
21) phenol and 7-bromoheptanol;
22) 4-chlorophenol and 7-bromoheptanol;
23) 4-chlorophenol and 6-bromohexanol;
24) 4-chlorophenol and 8-bromooctanol;
25) 4-chlorophenol and 9-bromonananol;
26) 2-chlorophenol and 8-bromooctanol;
27) 3-chlorophenol and 8-bromooctanol;
28) 1-hydroxynapthalene and 7-bromoheptanol;
29) 2-hydroxynapthalene and 7-bromoheptanol;
30) 3,5-bis(trifluoromethyl)phenol and 7-bromoheptanol;
31) 4-tert-butylphenol and 8-bromooctanol;
32) 4-phenylphenol and 8-bromooctanol;
33) 4-acetyl-3-methylphenol and 8-bromooctanol;
34) 3-pentyloxyphenol and 4-bromobutanol;
35) 4-chlorophenylthiol and 8-bromooctanol;
36) 4-chlorophenol and 10-bromodecanol;
37) 3,5-dimethoxyphenol and 8-bromooctanol;
38) 2,3,4-trichlorophenol and 8-bromooctanol;
39) 2,5-dinitrophenol and 8-bromooctanol;
40) 2,3-dimethylphenol and 8-bromooctanol;
41) 3,4-dimethylphenol and 8-bromooctanol;
42) 3-fluoro-4-nitrophenol and 8-bromooctanol;
43) 2,4-dimethylphenol and 8-bromooctanol;
44) 4-nitrophenol and 8-bromooctanol;
45) 3-nitrophenol and 8-bromooctanol;
46) 2,4-dinitrophenol and 8-bromooctanol;
47) 2,4-dichlorophenol and 8-bromooctanol;
48) 3-triflouromethoxyphenol and 8-bromooctanol;
49) 2-triflouromethylphenol and 8-bromooctanol;
50) 4-methoxyphenol and 8-bromooctanol;
51) 2-hydroxy-6-propoxynapthalene and 4-bromobutanol;
52) 2,3-dichlorophenol and 8-bromooctanol;
53) 2,5-dichlorophenol and 8-bromooctanol;
54) 4-methylphenol and 8-bromooctanol;
55) 4-triflouromethylphenol and 8-bromooctanol;
56) 2-nitrophenol and 8-bromooctanol;
57) 4-triflouromethoxyphenol and 8-bromooctanol;
58) 2,6-dichlorophenol and 8-bromooctanol;

are substituted for the 4-trifluoromethoxyphenol and the 8-bromooctanol in the above procedure, there is obtained:
21) 7-phenoxyheptanol;
22) 7-(4-chlorophenoxy)heptanol;
23) 6-(4-chlorophenoxy)hexanol;
24) 8-(4-chlorophenoxy)octanol;
25) 9-(4-chlorophenoxy)nonanol;
26) 8-(2-chlorophenoxy)octanol;
27) 8-(3-chlorophenoxy)octanol;
28) 7-(1-napthalenyloxy)heptanol;
29) 7-(2-napthalenyloxy)heptanol;
30) 7-(3,5-ditrifluoromethylphenoxy)heptanol;
31) 8-(4-tert-butylphenoxy)octanol;
32) 8-(4-phenylphenoxy)octanol;
33) 8-(4-acetyl-3-methylphenoxy)octanol;
34) 4-[3-(pentyloxy)phenoxy]butanol;
35) 8-[(4-chlorophenyl)thio]octanol;
36) 10-(4-chlorophenoxy)decanol;
37) 8-(3,5-dimethoxyphenoxy)octanol;
38) 8-(2,3,4-trichlorophenoxy)octanol;
39) 8-(2,5-dinitrophenoxy)octanol;
40) 8-(2,3-dimethylphenoxy)octanol;
41) 8-(3,4-dimethylphenoxy)octanol;
42) 8-(3-fluoro-4-nitrophenoxy)octanol;
43) 8-(2,4-dimethylphenoxy)octanol;
44) 8-(4-nitrophenoxy)octanol;
45) 8-(3-nitrophenoxy)octanol;
46) 8-(2,4-dinitrophenoxy)octanol;
47) 8-(2,4-dichlorophenoxy)octanol;
48) 8-(3-triflouromethoxyphenoxy)octanol;
49) 8-(2-triflouromethylphenoxy)octanol;
50) 8-(4-methoxyphenoxy)octanol;
51) 4-(6-propoxy-2-napthyloxy)butanol;
52) 8-(2,3-dichlorophenoxy)octanol;
53) 8-(2,5-dichlorophenoxy)octanol;
54) 8-(4-methylphenoxy)octanol;
55) 8-(4-triflouromethylphenoxy)octanol;
56) 8-(2-nitrophenoxy)octanol;
57) 8-(4-triflouromethoxyphenoxy)octanol;
58) 8-(2,6-dichlorophenoxy)octanol; respectively.

Step B. (R)-3-Carboxy-N,N,N-trimethyl-2-[[hydroxy{8-[(4-trifluoromethoxy)phenoxy]octyloxy}phosphinyl]oxy]-1-propanaminium Hydroxide, Inner Salt When the procedure of example 1 is carried out using an equivalent amount of the 8-(4-(trifluoromethoxy)-phenoxy)-1-octanol of step A of this example in place of the tetradecanol, there is obtained (R)-3-Carboxy-N,N,N-trimethyl-2-[[hydroxy{8-[4-(trifluoromethoxy)-phenoxy]octyloxy}phosphinyl]oxy]-1-propanaminium hydroxide, inner salt (m.p. ~174° C. [dec.]; $^{31}$P NMR=−1.156 ppm);

Following the procedure of example 1 and using an equivalent amount of the alcohols 21 through 58 of step A of this example in place of the tetradecanol, there is obtained:

21) (R)-3-Carboxy-N,N,N-trimethyl-2-{[hydroxy(7-phenoxyheptyloxy)phosphinyl]oxy}-1-propanaminium hydroxide, inner salt (m.p. ~160° C. [dec.]; $^{31}$P NMR=−0.812 ppm);

22) (R)-3-Carboxy-N,N,N-trimethyl-2-[{hydroxy[7-(4-chlorophenyoxy)heptyloxy]phosphinyl}oxy]-1-propanaminium hydroxide, inner salt (m.p. ~165° C. [dec.]; $^{31}$P NMR=0.036 ppm);

23) (R)-3-Carboxy-N,N,N-trimethyl-2-[{hydroxy[6-(4-chlorophenoxy)hexyloxy]phosphinyl}oxy]-1-propanaminium hydroxide, inner salt (m.p. ~165° C. [dec.]; $^{31}$P NMR=0.073 ppm);

24) (R)-3-Carboxy-N,N,N-trimethyl-2-[{hydroxy[8-(4-chlorophenoxy)octyloxy]phosphinyl}oxy]-1-propanaminium hydroxide inner salt (m.p. ~165° C. [dec.]; $^{31}$P NMR=0.326 ppm);

25) (R)-3-Carboxy-N,N,N-trimethyl-2-[{hydroxy[9-(4-chlorophenoxy)nonyloxy]phosphinyl}oxy]-1-propanaminium hydroxide, inner salt ($^{31}$P NMR=0.106 ppm);

26) (R)-3-Carboxy-N,N,N-trimethyl-2-[{hydroxy[8-(2-chlorophenoxy)octyloxy]phosphinyl}oxy]-1-propanaminium hydroxide, inner salt (m.p. ~173° C. [dec.]; $^{31}$P NMR=0.332 ppm);

27) (R)-3-Carboxy-N,N,N-trimethyl-2-[{hydroxy[8-(3-chlorophenoxy)octyloxy]phosphinyl}oxy]-1-propanaminium hydroxide, inner salt (m.p. ~180° C. [dec.]; $^{31}$P NMR=−1.166 ppm);

28) (R)-3-Carboxy-N,N,N-trimethyl-2-[{hydroxy[7-(1-napthalenyloxy)heptyloxy]phosphinyl}oxy]-1-propanaminium hydroxide, inner salt (m.p. ~165°–70° C. [dec.]; $^{31}$P NMR=0.162 ppm);

29) (R)-3-Carboxy-N,N,N-trimethyl-2-[{hydroxy[7-(2-napthalenyloxy)heptyloxy]phosphinyl}oxy]-1-propanaminium hydroxide, inner salt (m.p. ~170°–75° C. [dec.]; $^{31}$P NMR=0.142 ppm);

30) (R)-3-Carboxy-N,N,N-trimethyl-2-[[hydroxy{7-[3,5-(ditrifluoromethyl)phenoxy]heptyloxy}phosphinyl]oxy]-1-propanaminium hydroxide, inner salt (m.p. ~185° C. [dec.]; $^{31}$P NMR=0.153 ppm);

31) (R)-3-Carboxy-N,N,N-trimethyl-2-[[hydroxy{8-[4-(1,1-dimethylethyl)phenoxy]octyloxy}phosphinyl]oxy]-1-propanaminium hydroxide, inner salt (m.p. ~182° C. [dec.]; $^{31}$P NMR=0.337 ppm);

32) (R)-3-carboxy-N,N,N-trimethyl-2-[[hydroxy{8-[[(1,1'-biphenyl)-4-yl]oxy]octyloxy}phosphinyl]oxy]-1-propanaminium hydroxide, inner salt (m.p. ~190° C. [dec.]; $^{31}$P NMR=0.138 ppm);

33) (R)-3-carboxy-N,N,N-trimethyl-2-[[hydroxy{8-[(4-acetyl-3-methyl)phenoxy]octyloxy}phosphinyl]oxy]-1-propanaminium hydroxide, inner salt (m.p. ~172° C. [dec.]; $^{31}$P NMR=−1.214 ppm);

34) (R)-3-Carboxy-N,N,N-trimethyl-2-[[hydroxy{4-[3-(pentyloxy)phenoxy]butyloxy}phosphinyl]oxy]-1-propanaminium hydroxide, inner salt (m.p. ~190° C. [dec.]; $^{31}$P NMR=0.296 ppm);

35) (R)-3-Carboxy-N,N,N-trimethyl-2-[[hydroxy{8-[(4-chlorophenyl)thio]octyloxy}phosphinyl]oxy]-1-propanaminium hydroxide, inner salt (m.p. ~185° C. [dec.]; $^{31}$P NMR=0.269 ppm);

36) (R)-3-Carboxy-N,N,N-trimethyl-2-[{hydroxy[8-(4-chlorophenoxy)decyloxy]phosphinyl}oxy]-1-propanaminium hydroxide, inner salt (m.p. ~190° C. [dec.]; $^{31}$P NMR=0.109 ppm);

37) (R)-3-Carboxy-N,N,N-trimethyl-2-[{hydroxy[8-(3,5-dimethoxyphenoxy)octyloxy]phosphinyl}oxy]-1-propanaminium hydroxide, inner salt (m.p. ~159° C. [dec.]; $^{31}$P NMR=0.268 ppm);

38) (R)-3-Carboxy-N,N,N-trimethyl-2-[{hydroxy[8-(2,3,4-trichlorophenoxy)octyloxy]phosphinyl}oxy]-1-propanaminium hydroxide, inner salt (m.p. ~169° C. [dec.]; $^{31}$P NMR=0.264 ppm);

39) (R)-3-Carboxy-N,N,N-trimethyl-2-[{hydroxy[8-(2,5-dinitrophenoxy)octyloxy]phosphinyl}oxy]-1-propanaminium hydroxide, inner salt (m.p. 158° C. [dec.]; $^{31}$P NMR=0.131 ppm);

40) (R)-3-Carboxy-N,N,N-trimethyl-2-[{hydroxy[8-(2,3-dimethylphenoxy)octyloxy]phosphinyl}oxy]-1-propanaminium hydroxide, inner salt (m.p. 186°–8° C. [dec.]; $^{31}$P NMR=0.269 ppm; $[\alpha]^{25}=-8.08$ C=1.0 MeOH);

41) (R)-3-Carboxy-N,N,N-trimethyl-2-[{hydroxy[8-(3,4-dimethylphenoxy)octyloxy]phosphinyl}oxy]-1-propanaminium hydroxide, inner salt (m.p. ~190°–2° C. [dec.]; $^{31}$P NMR=0.321 ppm; $[\alpha]^{25}=-11.51$ C=1.0 MeOH);

42) (R)-3-Carboxy-N,N,N-trimethyl-2-[{hydroxy[8-(3-fluoro-4-nitrophenoxy)octyloxy]phosphinyl}oxy]-1-propanaminium hydroxide, inner salt (P$^{31}$ NMR=0.309 ppm; $[\alpha]^{25}=-7.70$ C=1.0 MeOH);

43) (R)-3-Carboxy-N,N,N-trimethyl-2-[{hydroxy[8-(2,4-dimethylphenoxy)octyloxy]phosphinyl}oxy]-1-propanaminium hydroxide, inner salt ($^{31}$P NMR=0.323 ppm; $[\alpha]^{25}=-9.69$ C=1.0 MeOH);

44) (R)-3-Carboxy-N,N,N-trimethyl-2-[{hydroxy[8-(4-nitrophenoxy)octyloxy]phosphinyl}oxy]-1-propanaminium hydroxide, inner salt (m.p. ~192°–4° C. [dec.]; $[\alpha]^{25}=-9.53$ C=1.0 MeOH);

45) (R)-3-Carboxy-N,N,N-trimethyl-2-[{hydroxy[8-(3-nitrophenoxy)octyloxy]phosphinyl}oxy]-1-propanaminium hydroxide, inner salt (m.p. ~174°–6° C. [dec.]; $^{31}$P NMR=0.097 ppm);

46) (R)-3-Carboxy-N,N,N-trimethyl-2-[{hydroxy[8-(2,4-dinitrophenoxy)octyloxy]phosphinyl}oxy]-1-propanaminium hydroxide, inner salt ($^{31}$P NMR=0.119 ppm; $[\alpha]^{25}=-9.14$ C=1.0 MeOH);

47) (R)-3-Carboxy-N,N,N-trimethyl-2-[{hydroxy[8-(2,4-dichlorophenoxy)octyloxy]phosphinyl}oxy]-1-propanaminium hydroxide, inner salt ($^{31}$P NMR=0.169 ppm; $[\alpha]^{25}=-6.84$ C=1.0 MeOH);

48) (R)-3-Carboxy-N,N,N-trimethyl-2-[{hydroxy[8-(3-triflouromethoxyphenoxy)octyloxy]phosphinyl}oxy]-1-propanaminium hydroxide, inner salt ($^{31}$P NMR=0.339 ppm; $[\alpha]^{25}=-7.96$ C=1.0 MeOH);

49) (R)-3-Carboxy-N,N,N-trimethyl-2-[{hydroxy[8-(2-triflouromethylphenoxy)octyloxy]phosphinyl}oxy]-1-propanaminium, hydroxide, inner salt (m.p. ~175°–7° C. [dec.]; $^{31}$P NMR=0.463 ppm; $[\alpha]^{25}=-8.50$ C=1.0 MeOH));

50) (R)-3-Carboxy-N,N,N-trimethyl-2-[{hydroxy[8-(4-methoxyphenoxy)octyloxy]phosphinyl}oxy]-1-propanaminium, hydroxide, inner salt ($^{31}$P NMR=0.333 ppm; $[\alpha]^{25}=-9.37$ C=1.0 MeOH));

51) (R)-3-Carboxy-N,N,N-trimethyl-2-[hydroxy{4-(6-propoxy-2-napthalenyloxy)butyloxy}phosphinyl]oxy-1-propanaminium, hydroxide, inner salt (m.p. ~163°–5° C. [dec.]; $^{31}$P NMR=0.295 ppm);

52) (R)-3-Carboxy-N,N,N-trimethyl-2-[{hydroxy[8-(2,3-dichlorophenoxy)octyloxy]phosphinyl}oxy]-1-propanaminium hydroxide, inner salt ($^{31}$P NMR=0.338 ppm; $[\alpha]^{25}=-8.25$ C=1.0 MeOH));

53) (R)-3-Carboxy-N,N,N-trimethyl-2-[{hydroxy[8-(2,5-dichlorophenoxy)octyloxy]phosphinyl}oxy]-1-propanaminium hydroxide, inner salt ($^{31}$P NMR=0.325 ppm; $[\alpha]^{25}=-7.69$ C=1.0 MeOH);

54) (R)-3-Carboxy-N,N,N-trimethyl-2-[{hydroxy[8-(4-methylphenoxy)octyloxy]phosphinyl}oxy]-1-propanaminium hydroxide, inner salt ($^{31}$P NMR=0.125 ppm; $[\alpha]^{25}$=−10.04 C=1.0 MeOH));

55) (R)-3-Carboxy-N,N,N-trimethyl-2-[{hydroxy[8-(4-triflouromethylphenoxy)octyloxy]phosphinyl}oxy]-1-propanaminium hydroxide, inner salt (m.p. ~186° C. [dec.]; $^{31}$P NMR=0.126 ppm; $[\alpha]^{25}$=−7.67 C=1.0 MeOH));

56) (R)-3-Carboxy-N,N,N-trimethyl-2-[{hydroxy[8-(2-nitrophenoxy)octyloxy]phosphinyl}oxy]-1-propanaminium hydroxide, inner salt [$^{31}$P NMR=0.339 ppm; $[\alpha]^{25}$=−8.56 C=1.0 MeOH)

57) (R)-3-Carboxy-N,N,N-trimethyl-2-[{hydroxy[8-(4-triflouromethoxyphenoxy)octyloxy]phosphinyl}oxy]-1-propanaminium hydroxide, inner salt (m.p. ~193°-5° C. [dec.]; $^{31}$P NMR=0.465 ppm; $[\alpha]^{25}$=−8.85 C=1.0 MeOH)); or 58) (R)-3-Carboxy-N,N,N-trimethyl-2-[{hydroxy[8-(2,6-dichlorophenoxy)octyloxy]phosphinyl}oxy]-1-propanaminium, hydroxide, inner salt ($^{31}$P NMR=0.340 ppm; $[\alpha]^{25}$=−8.61 C=1.0 MeOH)), respectively.

EXAMPLE 6

(R)-3-Carboxy-N,N,N-trimethyl-2-[[hydroxy{3-[3-(pentyloxy)phenoxy]propoxy}phosphinyl]oxy]-1-propanaminium Hydroxide, Inner Salt Step A 3-pentyloxyphenol A mixture of 24.8 ml of 1-Bromopentane, 66.0 g of resorcinol, and 41.5 g of potassium carbonate is stirred in 400 ml of anhydrous dimethylformamide at 60° C. for 17 hours. This mixture is filtered through Celite and concentrated under vacuum. The residue is taken up in water and extracted 3 times with ether. The combined extracts are washed with saturated sodium chloride, dried over magnesium sulfate, filtered, and concentrated under vacuum. The residue is flash chromatographed on normal phase silica gel eluting with a 4:1 ratio of hexane:ether to yield 3-pentyloxyphenol as a clear oil.

Step B 3-[3-(pentyloxy)phenoxy]propanol

A mixture of 0.80 g of 60% NaH in 28 ml of anhydrous dimethylformamide is cooled in an ice bath. To this is added 3.01 g of the above 3-pentyloxyphenol oil dissolved in 7 ml of anhydrous dimethylformamide. This mixture is then stirred at room temperature for 45 minutes; 1.81 ml of 3-Bromopropanol are added; and the resultant mixture is stirred at 60° C. for 17 hours. The solvent is removed under vacuum, and the residue worked up in same manner as above. The residue obtained is flash chromatographed on normal phase silica gel eluting with a 3:2 ratio of hexane:ether to yield 3-[3-(pentyloxy)phenoxy]propanol as a pale yellow oil.

When an equivalent amount of:

59) 1-bromohexane and 3-bromopropanol;
60) 1-bromobutane and 5-bromopentanol; or
61) 1-bromopentane and 5-bromopentanol, are substituted for the 1-bromopentane and 3-bromopropanol in Steps A and B of the above procedure, there is obtained 59) 3-[3-(hexyloxy)phenoxy]propanol;
60) 5-[3-(butyloxy)phenoxy]pentanol; or
61) 5-[3-(pentyloxy)phenoxy]pentanol, respectively.

Step C. (R)-3-Carboxy-N,N,N-trimethyl-2-[[hydroxy{3-[3-(pentyloxy)phenoxy]propyloxy}phosphinyl]oxy]-1-propanaminium Hydroxide, Inner Salt When the procedure of example 1 is carried out using an equivalent amount of the 3-[3-(pentyloxy)phenoxy]propanol of step A of this example in place of the tetradecanol, there is obtained (R)-3-Carboxy-N,N,N-trimethyl-2-[[hydroxy{3-[3-(pentyloxy)phenoxy]propoxy}phosphinyl]oxy]-1-propanaminium hydroxide, inner salt ($^{31}$P NMR=−0.745 ppm).

Following the procedure of example 1 and using an equivalent amount of the alcohols 59 through 61 of step A of this example in place of the tetradecanol, there is obtained:

59) (R)-3-Carboxy-N,N,N-trimethyl-2-[[hydroxy{3-[3-(hexyloxy)phenoxy]propyloxy}phosphinyl]oxy]-1-propanaminium hydroxide, inner salt (m.p. 150° [semi-liquid]−~195° C. [dec.]; $^{31}$P NMR=0.182 ppm);

60) (R)-3-Carboxy-N,N,N-trimethyl2-[[hydroxy{5-[3-(butyloxy)phenoxy]pentyloxy}phosphinyl]oxy]-1-propanaminium hydroxide, inner salt ($^{31}$P NMR=−0.591 ppm); or 61) (R)-3-Carboxy-N,N,N-trimethyl-2-[[hydroxy{5-[3-(pentyloxy)phenoxy]pentyloxy}phosphinyl]oxy]-1-propanaminium hydroxide, inner salt, ($^{31}$P NMR=−0.737 ppm), respectively.

EXAMPLE 7

(R)-3-Carboxy-N,N,N-trimethyl-2-[[hydroxy{4-[3-(pentyloxy)phenoxy]butoxy}phosphinyl]oxy]-1-propanaminium Hydroxide, Inner Salt Step A. 4-[3-(pentyloxy)phenoxy]butanol A mixture of 7.3 g of 60% NaH in 190 ml of anhydrous dimethylformamide is cooled in an ice bath. To this mixture is added 22.0 g of 3-pentyloxyphenol dissolved in 50 ml of anhydrous dimethylformamide. This mixture is then stirred at room temperature for 45 minutes; 23.2 ml of ethyl 4-bromobutyrate are added; and the resultant mixture is stirred at 60° C. for 17 hours. The solvent is removed under vacuum and the residue worked up as above. The residue is flash chromatographed on normal phase silica gel using a gradient from hexane to a 4:1 ratio of hexane:ether to yield ethyl 4-(3-pentyloxyphenoxy)butyrate as a clear oil.

To a suspension of 6.8 g of lithium aluminum hydride in 200 ml of anhydrous ether are added 26.2 g of ethyl 4-(3-pentyloxyphenoxy)butyrate dissolved in 100 ml of anhydrous ether. Addition is carried out at a rate which maintains reflux of the solvent. After 30 minutes, the mixture is cooled in an ice bath and quenched with water. 3N HCl is added; and the organic layer is separated, dried over magnesium sulfate, filtered, and concentrated under vacuum to yield 4-[3-(pentyloxy)phenoxy]butanol.

When an equivalent amount of:

62) 1-bromohexane or
63) 1-bromobutane is substituted for the 1-bromopentane in Step A of Example 6 and an equivalent amount of the product obtained is used in place of the above 3-pentyloxyphenol, there is obtained:

62) 4-[3-(hexyloxy)phenoxy]butanol or
63) 4-[3-(butyloxy)phenoxy]butanol, respectively.

When an equivalent amount of:

64) 5-methylresorcinol;
65) 5-methoxyresorcinol;

66) 2,4-dichlororesorcinol;
67) 2-methylresorcinol; or
68) 3-cyanoresorcinol;

is used in place of the resorcinol or equivalent amounts of: 1-bromobutane and hydroquinone are used in place of the 1-bromopentane and resorcinol in Step A of Example 6; and an equivalent amount of the product obtained is used in place of the above 3-pentyloxyphenol of this example, there is obtained:

64) 4-[5-(methyl)-3-(pentyloxy)phenoxy]butanol;
65) 4-[5-(methoxy)-3-(pentyloxy)phenoxy]butanol;
66) 4-[2,4-(dichloro)-5-(pentyloxy)phenoxy]butanol;
67) 4-[2-(methyl)-3-(pentyloxy)phenoxy]butanol;
68) 4-[3-(cyano)-5-(pentyloxy)phenoxy]butanol;
69) 4-[4-(butyloxy)phenoxy)butanol, respectively.

When an equivalent amount of 1-bromopropane and 2,7-dihydroxynapthalene or 1-bromobutane and 1,5-dihydroxynaphthylene are substituted for the 1-bromopentane and the resorcinol in the procedure of Step A of Example 6, and an equivalent amount of the product obtained is used in place of the above 3-pentyloxyphenol of this example, there is obtained:

70) 4-[7-(propoxy)-2-naphthalenyloxy]butanol or
71) 4-[5-(butoxy)-1-naphthalenyloxy]butanol, respectively.

Step B. (R)-3-Carboxy-N,N,N-trimethyl-2-[[hydroxy{4-[3-(pentyloxy)phenoxy]butyloxy}phosphinyl]oxy]-1-propanaminium Hydroxide, Inner Salt When the procedure of example 1 is carried out using an equivalent amount of the 4-[3-(pentyloxy)phenoxy]butanol of step A of this example in place of the tetradecanol, there is obtained (R)-3-Carboxy-N,N,N-trimethyl-2-[[hydroxy{4-[3-(pentyloxy)phenoxy]butoxy}phosphinyl]oxy]-1-propanaminium hydroxide, inner salt (m.p. ~190° C. [dec.]; $^{31}$P NMR=0.296 ppm).

Following the procedure of example 1 and using an equivalent amount of the alcohols 62 through 71 of step A of this example in place of the tetradecanol, there is obtained:

62) (R)-3-Carboxy-N,N,N-trimethyl-2-[[hydroxy{4-[3-(hexyloxy)phenoxy]butyloxy}phosphinyl]oxy]-1-propanaminium hydroxide, inner salt (m.p. 150° [semi-liquid]—~192° C. [dec.]; $^{31}$P NMR=0.281 ppm);
63) (R)-3-Carboxy-N,N,N-trimethyl-2-[[hydroxy{4-[3-(butyloxy)phenoxy]butyloxy}phosphinyl]oxy]-1-propanaminium hydroxide, inner salt ($^{31}$P NMR=—0.752 ppm);
64) (R)-3-Carboxy-N,N,N-trimethyl-2-[[hydroxy{4-[5-(methyl)-3-(pentyloxy)phenoxy]butyloxy}phosphinyl]oxy]-1-propanaminium hydroxide, inner salt ($^{31}$P NMR=0.247 ppm);
65) (R)-3-Carboxy-N,N,N-trimethyl-2-[[hydroxy{4-[5-(methoxy)-3-(pentyloxy)phenoxy]butyloxy}phosphinyl]oxy]-1-propanaminium hydroxide, inner salt (m.p. ~179°–81° C. [dec.]; $^{31}$P NMR=0.381 ppm);
66) (R)-3-Carboxy-N,N,N-trimethyl-2-[[hydroxy{4-[2,4-(dichloro)-5-(pentyloxy)phenoxy]butyloxy}phosphinyl]oxy]-1-propanaminium hydroxide, inner salt (m.p. ~173°–5° C. [dec.]; $^{31}$P NMR=0.250 ppm);
67) (R)-3-Carboxy-N,N,N-trimethyl-2-[[hydroxy{4-[2-(methyl)-3-(pentyloxy)phenoxy]butyloxy{phosphinyl]oxy]-1-propanaminium hydroxide, inner salt ($^{31}$P NMR=0.293 ppm; [α]$^{25}$=—9.24 C=1.0 MeOH));
68) (R)-3-Carboxy-N,N,N-trimethyl-2-[[hydroxy{4-[3-(cyano)-5-(pentyloxy)phenoxy]butyloxy}phosphinyl]oxy]-1-propanaminium hydroxide, inner salt ($^{31}$P NMR=—0.866 ppm; [α]$^{25}$=—6.96 C=0.99 MeOH));
69) (R)-3-Carboxy-N,N,N-trimethyl-2-[[hydroxy{4-[4-(butyloxy)phenoxy]butyloxy}phosphinyl]oxy]-1-propanaminium hydroxide, inner salt ($^{31}$P NMR=3.299 ppm);
70) (R)-3-Carboxy-N,N,N-trimethyl-2-[[hydroxy{4-[7-(propoxy)-2-naphthalenyloxy]butyloxy}phosphinyl]oxy]-1-propanaminium hydroxide, inner salt (m.p. ~175° C. [dec.]; $^{31}$P NMR=0.278 ppm); or
71) (R)-3-Carboxy-N,N,N-trimethyl-2-[[hydroxy{4-[5-(butoxy)-1-naphthalenyloxy]butyloxy}phosphinyl]oxy]-1-propanaminium hydroxide, inner salt (m.p. ~180° C. [dec.]; $^{31}$P NMR=0.046 ppm), respectively.

EXAMPLE 8

(R)-3-Carboxy-N,N,N-trimethyl-2-{[hydroxy(tetradecyloxy)phosphinothioyl]oxy}-1-propanaminium, Hydroxide, Inner Salt To a solution of 7.8 gm of the tetrafluoroborate salt of L-carnitine and 11.2 gm of collidine in 100 ml of acetonitrile is added 14.7 gm of dichlorotetradecylphosphite in 50 ml of acetonitrile. The reaction mixture is stirred at room temperature for 1.5 hours and then the solvents are removed under vacuum. The resulting residue is dissolved in a mixture of 400 ml of pyridine and 20 ml of water that had been saturated with nitrogen gas and is stirred under a nitrogen atmosphere at room temperature for 30 minutes. Next, 7.4 gm of sulfur is added and the mixture is stirred for a further 18 hours. The reaction mixture is filtered through Celite, and the filtrate is concentrated under vacuum. The resulting residue is flash chromatographed on silica gel, initially with a 50/30/3 ratio of methylene chloride/methanol/concentrated ammonium hydroxide and then with a 50/30/5 ratio of-the same solvent system to give a diastereomeric mixture of the desired material. Additional low pressure chromatography using a 300/400/60/72 ratio of hexane/isopropanol/water/isopropylamine yielded crude isomer A and isomer B. The individual isomers were further purified by flash chromatography on silica gel eluting initially with a 50/30/3 ratio of methylene chloride/methanol/concentrated ammonium hydroxide and then with a 50/30/6 ratio of the same solvent system. Further purification was achieved by flash chromatography on LiChroprep RP-8 silica gel, eluting initially with water and then with ethanol, to give the pure individual diastereomers as amorphous solids:

Isomer A—$^{31}$P NMR=57.5 ppm; [α]$^{25}$=—21.3 C=1.0 MeOH,
Isomer B—$^{31}$P NMR=115.3 ppm; [α]$^{25}$=—14.8 C=1.0 MeOH).

Following the above procedure, but using an equivalent amount of 72) dichloro-4-[3-(pentyloxy)phenoxy]butyl phosphite;
73) dichloro-4-[5-(methyl)-3-(pentyloxy)phenoxy]butyl phosphite;
74) dichloro-8-[4-(triflouromethoxy)phenoxy]octyl phosphite; or
75) dichloro-4-[3-(hexyloxy)phenoxy]butyl phosphite, in place of the dichlorotetradecylphosphite, there is obtained 72 (R)-3-carboxy-N,N,N-trimethyl-2-[[hydroxy{4-[3-(pentyloxy)phenoxy]butyloxy}phosphinothioyl]oxy]-1-propanaminium hydroxide, inner salt;

73 (R)-3-carboxy-N,N,N-trimethyl-2-[[hydroxy{4-[5-(methyl)-3-(pentyloxy)-phenoxy]butyloxy}phosphinothioyl]oxy]-1-propanaminium hydroxide inner salt;

74 (R)-3-carboxy-N,N,N-trimethyl-2-[[hydroxy{8-[4-(triflouromethoxy)phenoxy]octyloxy}phosphinothioyl]oxy]-1-propanaminium hydroxide, inner salt; or 75 (R)-3-carboxy-N,N,N-trimethyl-2-[[hydroxy{4-[3-(hexyloxy)phenoxy]butyloxy}phosphinothioyl]oxy]-1-propanaminium hydroxide, inner salt, respectively.

The above inner salts are separated by chromatography into the following diastereoisomers:

72) isomer A ($^{31}$P NMR=57.8 ppm; $[\alpha]^{25}=-17.7$ C=1.0 MeOH) and isomer B ($^{31}$P NMR=58.3 ppm; $[\alpha]^{25}=-12.1$ C=1.0 MeOH);

73) isomer A (m.p. ~155°-9° C.; $^{31}$P NMR=57.9 ppm; $[\alpha]^{25}=-20.1$ C=1.0 MeOH) and isomer B (m.p. ~153°-168° C.; $^{31}$P NMR=58.3 ppm; $[\alpha]^{25}=-13.0$ C=1.0 MeOH);

74) isomer A (m.p. ~157°-161° C.; $^{31}$P NMR=57.8 ppm; $[\alpha]^{25}=-18.8$ C=1.0 MeOH) and isomer B (m.p. ~148°-160° C.; $^{31}$P NMR=58.2 ppm; $[\alpha]^{25}=-12.9$ C=1.0 MeOH) and 75) isomer A ($^{31}$P NMR=57.7 ppm; $[\alpha]^{25}=-19.8$ C=1.0 MeOH) and isomer B ($^{31}$P NMR=58.3 ppm; $[\alpha]^{25}=-12.8$ C=1.0 MeOH).

The phosphite starting materials for compounds 74 to 77 are prepared as in Example 1 using in place of tetradecanol the alcohols of Examples 7 (title compound), 7 (compound 66), 5 (title compound), and 7 (compound 64).

EXAMPLE 9

(R)-3-Carboxy-N,N,N-trimethyl-2-[{mercapto(tetradecyloxy)phosphinothioyl}oxy]-1-propanaminium, Hydroxide, Inner Salt To a solution of 1.2 gm of the tetrafluoroborate salt of L-carnitine and 1.7 gm of collidine in 10 ml of acetonitrile is added 5.7 gm of dichlorotetradecylphosphite in 15 ml of acetonitrile. The reaction mixture is stirred at room temperature for 1 hour, and then hydrogen sulfide gas is bubbled through the mixture for five minutes. The reaction mixture is stirred at room temperature an additional fifteen minutes, and then the solvents are removed under vacuum. The resulting residue is dissolved in 50 ml of pyridine and 1 ml of water and 1.1 gm of sulfur is added, and the mixture is stirred at room temperature for 17 hours. The reaction mixture is filtered through Celite and the filtrate is concentrated under vacuum. The resulting residue is flash chromatographed on silica gel, initially with a 50/30/5 ratio of methylene chloride/methanol/concentrated ammonium hydroxide and then with a 50/30/5 ratio of the same solvent system. Subsequent flash chromatography on LiChroprep RP-8 silica gel eluting initially with water and then with methanol gave (R)-3-Carboxy-N,N,N-trimethyl-2-[{mercapto(tetradecyloxy)phosphinothioyl}oxy]-1-propanaminium, sulfide, inner salt as an amorphous solid (m.p. ~178° C. [dec.]; $^{31}$P NMR=115.3 ppm).

Following the above procedure, but using an equivalent amount of 72) dichloro-4-[3-(pentyloxy)phenoxy]butyl phosphite, in place of the dichlorotetradecylphosphite, there is obtained 76) (R)-3-carboxy-N,N,N-trimethyl-2-[[mercapto{4-[3-(pentyloxy)phenoxy]butyloxy}phosphinothioyl]oxy]-1-propanaminium hydroxide, inner salt (m.p. ~85°-105° C.; $^{31}$P NMR=115.6 ppm; $[\alpha]^{25}=-17.5$ C=1.0 MeOH)).

EXAMPLE 10

(R)-3-Carboxy-N,N,N-trimethyl-2-[{2-(propenyl)oxy[tetradecyloxy]phosphinyl}oxy]-1-propanaminium Hydroxide, Inner Salt To a solution of 2.0 gms of the tetrafluoroborate salt of L-carnitine in 32 ml of acetonitrile and 3.2 ml of collidine, 3.8 gms of dichlorotetradecylphosphite are added and the reaction mixture is stirred at room temperature for 24 hours. To this is then added 2.7 ml of allyl alcohol and the solution is stirred at room temperature for 2 hours. A solution of 2.6 gms of NaIO$_4$ in 10.0 ml of water is added and the reaction mixture is stirred for 2 hours. The mixture is then filtered through Celite, which is subsequently washed with methanol and concentrated under vacuum to give a white, oily solid. This is flash chromatographed, initially with a 50/10/0.5 ratio of chloroform/methanol/concentrated ammonium hydroxide and subsequently with a 50/30/3 ratio. The ammonium hydroxide salt was then flash chromatographed through a reverse phase plug (LiChroprep RP-8 silica gel) to give 3-Carboxy-N,N,N-trimethyl-2-[{2-(propenyl)oxy[tetradecyloxy]phosphinyl}oxy]-1-propanaminium hydroxide, inner salt as an off-white solid (m.p. ~100° [softens]—~120° C. [clear oil]; $^{31}$P NMR=−1.280, −1.315 ppm).

EXAMPLE 11

(R)-N,N,N-trimethyl-4-oxo-4-[(2-propenyl)oxy]-2-[{hydroxy(tetradecyloxy)phosphinyl}oxy]-1-butanaminium Hydroxide, Inner Salt To a solution of 3.6 gm of the tetrafluoroborate salt of the allyl ester of L-carnitine and 4.5 gm of collidine in 25 ml of acetonitrile is added 5.7 gm of dichlorotetradecylphosphite in 25 ml of acetonitrile. The reaction mixture is stirred at room temperature for 17 hours, and then a solution of 4 gm of sodium metaperiodate in 20 ml of water is added. After stirring at room temperature for two hours, the reaction mixture is filtered through Celite; and the filtrate is concentrated under vacuum. The resulting residue is flash chromatographed on silica gel, initially with a 50/30/5 ratio of methylene chloride/methanol/concentrated ammonium hydroxide and then with a 50/30/8 ratio of the same solvent system. Subsequent flash chromatography on LiChroprep RP-8 silica gel eluting initially with water and then with methanol gave N,N,N-trimethyl-4-oxo-4-[(2-propenyl)oxy]-2-[{hydroxy(tetradecyloxy)phosphinyl}oxy]-1-butanaminium hydroxide, inner salt as an amorphous solid ($^{31}$P NMR=0.108 ppm).

EXAMPLE 12

(R)-3-carboxy-N,N,N-trimethyl-2-[[hydroxy{4-[4-(phenoxy)phenoxy]butyloxy}phosphin]oxy]-1-propanaminium Hydroxide, Inner Salt Step A. Ethyl 4-((4-phenoxy)phenoxy)butyrate A mixture of 5.59 g (30.0 moles) of 4-(phenoxy)phenol, 5.75 g (29.5 moles) of ethyl 4-bromobutyrate, and 8.29 g (60.0 mmoles) of $K_2CO_3$ in 30 ml of anhydrous dimethylformamide are stirred at room temperature for 96 hrs. The reaction mixture is then poured into water and extracted two times with ether. The combined ether extracts are washed with water followed by brine and dried over $MgSO_4$. After filtration and concentration, the crude title product is purified by flash chromatography on silica gel, eluting with a 20:1 hexane/ethyl acetate mixture followed by a 12:1 mixture.

Step B. 4-((4-Phenoxy)phenoxy)butanol

Into a 3-neck flask containing 100 ml of anhydrous ethyl ether under a $N_2$ atmosphere, is added 1.91 g of lithium aluminum hydride (50.4 mmoles). A solution of 7.55 g (25.2 mmoles) of ethyl 4-((4-phenoxy)phenoxy)butyrate in 25 ml of anhydrous ethyl ether is then added at a rate which maintains a gentle reflux. Upon completion of the addition, the reaction is stirred at ambient temperature for 96 hrs. and then quenched by the careful addition of 2 ml of water, 4 ml of 2N NaOH solution, and 4 ml of water. The white solid which forms is removed by filtration, and the filtrate is dried over $MgSO_4$. Filtration and concentration yields the title compound.

Step C. (R)-3-Carboxy-N,N,N-trimethyl-2-[[hydroxy{4-[4-(phenoxy)phenoxy]butoxy}phosphinyl]oxy]-1-propanaminium Hydroxide, Inner Salt When the procedure of example 1 is carried out using an equivalent amount of the 4-[4-(phenoxy)phenoxy]-butanol of step B of this example in place of the tetradecanol, there is obtained (R)-3-Carboxy-N,N,N-trimethyl-2-[[hydroxy{4-[4-(phenoxy)phenoxy]butoxy}phosphinyl]oxy]-1-propanaminium hydroxide, inner salt ($^{31}P$ NMR=0.074 ppm; $[\alpha]^{25}=-8.84$ C=1.0 MeOH)).

Following the above procedure, but using an equivalent amount of 77) 3-(phenoxy)phenol;
78) 3-(4-triflouromethoxyphenoxy)phenol;
79) 4-(4-triflouromethoxyphenoxy)phenol;
80) 4-(1-naphthoxy)phenol; or
81) 3-(2-naphthoxy)phenol, in place of the 4-(phenoxy)phenol in step A, there is obtained 77) (R)-3-Carboxy-N,N,N-trimethyl-2-[[hydroxy{4-[3-(phenoxy)phenoxy]butoxy}phosphinyl]oxy]-1-propanaminium hydroxide, inner salt ($^{31}P$ NMR=0.170 ppm; $[\alpha]^{25}=-7.74$ C=1.0 MeOH));
78) (R)-3-Carboxy-N,N,N-trimethyl-2-[[hydroxy{4-[3-(4-triflouromethoxyphenoxy)phenoxy]butoxy}phosphinyl]oxy]-1-propanaminium hydroxide, inner salt (m.p. 184°–6° C. [dec.]; $^{31}P$ NMR=0.286 ppm; $[\alpha]^{25}=-7.51$ C=1.0 MeOH));
79) (R)-3-Carboxy-N,N,N-trimethyl-2-[[hydroxy{4-[4-(4-triflouromethoxyphenoxy)phenoxy]butoxy}phosphinyl]oxy]-1-propanaminium hydroxide, inner salt ($^{31}P$ NMR=0.078 ppm; $[\alpha]^{25}=-7.54$ C=1.0 MeOH));
80) (R)-3-Carboxy-N,N,N-trimethyl-2-[[hydroxy{4-[4-(1-naphthoxy)phenoxy]butoxy}phosphinyloxy]-1-propanaminium hydroxide, inner salt (m.p. ~170° C. [dec.]; $^{31}P$ NMR=0.082 ppm); or
81) (R)-3-Carboxy-N,N,N-trimethyl-2-[[hydroxy{4-[3-(2-naphthoxy)phenoxy]butoxy}phosphinyl]oxy]-1-propanaminium hydroxide, inner salt (m.p. ~175° C. [dec.]; $^{31}P$ NMR=0.060 ppm), respectively.

EXAMPLE 13

(R)-3-Carboxy-N,N,N-trimethyl-2-[{hydroxy[(N-ethyl-N-heptyl)hexamidyl-6-oxyl]phosphinyl}oxy]-1-propanaminium Hydroxide, Inner Salt Step A. N-heptyl-N-ethyl(6-hydroxy)hexanamide Step A. To a solution of 5.0 gms of 1-aminoheptane in 150 ml of $CH_2Cl_2$, is added 10.9 ml of $Et_3N$ followed by 2.79 ml of acetyl chloride. The reaction mixture is stirred at room temperature for 18 hours and then concentrated under vacuum. The residue obtained is partitioned between ethyl acetate and an aqueous 2N HCl solution; and after separating, the organic layer is washed with aqueous saturated $NaHCO_3$, then brine, and dried over $Na_2SO_4$. After filtration and concentration, N-heptylacetamide is obtained as a clear liquid.

A mixture of a solution of 5.5 gms of the N-heptylacetamide in 150 ml of diethyl ether and 3.99 gms of lithium aluminum hydride are stirred at room temperature for 18 hours. The reaction mixture is then worked up with $H_2O$/NaOH by the Fieser method, following which the organic layer is dried over $MgSO_4$, filtered, and concentrated under vacuum to give N-heptyl-N-ethylamine.

To a solution of 3.2 gms of the N-heptyl-N-ethylamine in 96 ml of $CH_2Cl_2$ are added 5.7 ml of $Et_3$ followed by 3.63 ml of hexanedioic acid monochloride monomethyl ester. This mixture is stirred at room temperature for 18 hours; and after concentrating under vacuum, the residue obtained is partitioned between ethyl acetate and an aqueous 2N HCl solution. The organic layer is separated and washed with aqueous saturated $NaHCO_3$, then brine, and dried over $MgSO_4$. Following filtration and concentration under vacuum, the residue is flash chromatographed on normal phase silica gel using a 3/1 ratio of hexane and ethyl acetate to yield N-heptyl-N-ethyladipamic acid, methyl ester.

A mixture of a solution of 3.1 gms of the N-heptyl-N-ethyladipamic acid, methyl ester in 40 ml of tert-butanol and 800 mg of sodium borohydride is heated to reflux, following which 7.8 ml of methanol is added dropwise. The reaction mixture is stirred at reflux for 18 hours and then partitioned between water and $CH_2Cl_2$. After separation, the organic layer is dried over $MgSO_4$, filtered, and concentrated under vacuum. The residue obtained is flash chromatographed on normal phase silica gel with a 4/1 ratio of hexane and ethyl acetate to yield 1.0 gms of N-heptyl-N-ethyl(6-hydroxy)hexanamide.

When the above procedure is carried out using an equivalent amount of

82) N-heptyl-N-methylamine and hexanedioic acid monochloride monomethyl ester;
83) N-hexyl-N-methylamine and heptanedioic acid monochloride monomethyl ester; or
84) N-[2-(4-chlorophenoxy)ethyl]-N-methylamine and hexanedioic acid monochloride monomethyl ester, in place of the N-heptyl-N-ethylamine and hexanedioic acid monochloride monomethyl ester, there is obtained
82) N-heptyl-N-methyl-6-hydroxyhexanamide;

83) N-hexyl-N-methyl-7-hydroxyheptanamide; or
84) N-[2-(4-chlorophenoxy)ethyl]-N-methyl-6-hydroxyhexanamide, respectively.

B. (R)-3-Carboxy-N,N,N-trimethyl-2-[{hydroxy[(N-ethyl-N-heptyl)hexamidyl-6-oxyl]phosphinyl}oxy]-1-propanaminium Hydroxide, Inner Salt A solution containing 1.45 gms of the tetrafluoroborate salt of carnitine and 2.05 ml of collidine in 20 ml of acetonitrile is cooled to −40° C., and 0.34 ml. of phosphorous trichloride is syringe-added. The reaction is stirred at −40° C. for 10 min. and then at ice-water temperature for 2 hours. A solution of 1.0 gms of N-heptyl-N-ethyl(6-hydroxy)-hexanamide in 4.0 ml of tetrahydrofuran is syringe-added, and the reaction mixture is stirred at ice-water temperature for 2 hours. To this mixture is added a solution of 0.83 gms of NaIO$_4$ in 3 ml of water, following which it is stirred at room temperature for 18 hours and then concentrated under vacuum. The residue obtained is flash chromatographed, initially with a 50/30/3 ratio of CH$_2$Cl$_2$/MeOH/NH$_4$OH and then, after filtering off the non-polar impurities, with a 50/30/10 ratio. The isolated ammonium hydroxide inner salt is then flash chromatographed through a reverse phase plug (LiChroprep RP-8 silica gel) to yield the title compound as a light yellow solid (m.p. ∼175° C. [dec.]; $^{31}$P NMR = −0.046 ppm).

Following the above procedure, but using an equivalent amount of

82) N-heptyl-N-methyl-6-hydroxyhexanamide;
83) N-hexyl-N-methyl-7-hydroxyheptanamide; or
84) N-[2-(4-chlorophenoxy)ethyl]-N-methyl-6-hydroxyhexanamide, in place of the N-heptyl-N-ethyl-6-hydroxyhexanamide, there is obtained 82) (R)-3-Carboxy-N,N,N-trimethyl-2-[{hydroxy[(N-methyl-N-heptyl)hexamidyl-6-oxyl]phosphinyl}oxy]-1-propanaminium hydroxide, inner salt ($^{31}$P NMR=0.008 ppm);
83) (R)-3-Carboxy-N,N,N-trimethyl-2-[{hydroxy[(N-methyl-N-hexyl)heptamidyl-7-oxyl]phosphinyl}oxy]-1-propanaminium hydroxide, inner salt (m.p. ∼155° C. [dec.]; $^{31}$P NMR=0.092 ppm); or
84) (R)-3-Carboxy-N,N,N-trimethyl-2-[[hydroxy{N-methyl-N-[2-(4-chlorophenoxy)ethy]hexamidyl-6-oxyl}phosphinyl]oxy]-1-propanaminium hydroxide, inner salt (m.p. ∼180° C. [dec.]; $^{31}$P NMR=0.038 ppm), respectively.

EXAMPLE 14

(R)-3-Carboxy-N,N,N-trimethyl-2-[{hydroxy[(N-methyl-N-hexanoyl)-7-aminoheptyloxy]phosphinyl}oxy]-1-propanaminium Hydroxide, Inner Salt Step A. N-(7-hydroxyheptyl) N-methylhexamide A solution of 5.0 gms of 7-bromoheptanol in 8 ml of dioxane and 57 ml of a 40% by weight aqueous solution of methylamine in a sealed glass bomb is stirred at 60° C. for 16 hours. The reaction mixture is then cooled and concentrated to give a quantitative yield of the HBr salt of 7-(N-methylamino)heptanol.

To a solution containing 6.2 gms of the HBr salt of 7-(N-methylamino)heptanol and 10.9 ml of Et$_3$N in 170 ml of CH$_2$Cl$_2$ cooled to ice-water temperature, 5.46 ml of hexanoylchloride is syringe-added; and the reaction is stirred at room temperature for 18 hours. The mixture is then acidified with 2N HCl; and after extraction with methylene chloride, the organic layer is washed with aqueous saturated NaHCO$_3$, and then brine, dried over MgSO$_4$, filtered, and concentrated under vacuum. The residue obtained is flash chromatographed on normal phase silica gel starting with a 4/1 ratio of hexane and ethyl acetate and ending with a ¼ hexane/ethyl acetate ratio to yield N-(7-hydroxyheptyl) N-methylhexamide.

When the above procedure is carried out using an equivalent amount of 85) 6-bromohexanol and heptanoylchloride;
86) 5-bromopentanol and heptanoylchloride; or
87) 6-bromohexanol and 2-(4-chlorophenoxy)-acetylchloride, in place of the 7-bromoheptanol and hexanoylchloride, there is obtained 85) N-(6-hydroxyhexyl)-N-methylheptamide;
86) N-(5-hydroxypentyl)-N-methylheptamide; or
87) N-(6-hydroxyhexyl)-N-methyl-2-(4-chlorophenoxy)acetamide, respectively.

Step B. (R)-3-Carboxy-N,N,N-trimethyl-2-[{hydroxy[(N-methyl-N-hexanoyl)-7-aminoheptyloxy]phosphinyl}oxy]-1-propanaminium, Hydroxide, Inner Salt When the procedure of Step B of Example 13 is carried out using an equivalent amount of the N-(7-hydroxyheptyl)- N-methylhexamide of step A of this example in place of the N-heptyl-N-ethyl(6-hydroxy) hexamide there is obtained (R)-3-Carboxy-N,N,N-trimethyl-2-[{hydroxy[(N-methyl-N-hexanoyl)-7-aminoheptyloxy]phosphinyl}oxy]-1-propanaminium hydroxide, inner salt (m.p. ∼180° C. [dec.]; $^{31}$P NMR=0.115 ppm).

Following the above procedure, but using an equivalent amount of

85) N-(6-hydroxyhexyl)-N-methylheptamide;
86) N-(5-hydroxypentyl)-N-methylheptamide; or
87) N-(6-hydroxyhexyl)-N-methyl-2-(4-chlorophenoxy)acetamide, in place of the N-(7-hydroxyheptyl)-N-methylhexamide there is obtained 85) (R)-3-Carboxy-N,N,N-trimethyl-2-[{hydroxy[(N-methyl-N-heptanoyl)-6-aminohexyloxy]phosphinyl}oxy]-1-propanaminium hydroxide, inner salt (m.p. ∼175° C. [dec.]; $^{31}$P NMR=0.308 ppm);
86) (R)-3-Carboxy-N,N,N-trimethyl-2-[{hydroxy[(N-methyl-N-heptanoyl)-5-aminopentyloxy]phosphinyl}oxy]-1-propanaminium hydroxide, inner salt (m.p. ∼175° C. [dec.]; $^{31}$P NMR=0.086 ppm); or
87) (R)-3-Carboxy-N,N,N-trimethyl-2-[{hydroxy[{N-methyl-N-[2-(4-chlorophenoxy)acety]}-6-aminohexyloxy]phosphinyl}oxy]-1-propanaminium Hydroxide, Inner Salt (m.p. ∼175° C. [dec.]; $^{31}$P NMR=0.125 ppm), respectively.

EXAMPLE 15

(R)-3-Carboxy-N,N,N-trimethyl-2-[[hydroxy{5-[3-(pentyloxy)phenyl]pentyl]oxy}phosphinyl]oxy]-1-propanaminium Hydroxide, Inner Salt Step A. 3-(5-hydroxypentyl)-phenol, n-pentyl Ether To a solution of 5.0 gm of 3-Bromophenol in 60 mls of dimethylformamide is added 6.0 gm of potassium carbonate followed by 4.3 ml of 1-bromopentane. This mixture is heated to 60° C. for 6 hours and then cooled to room temperature and filtered. The filtrate is diluted with ether and washed with water and brine. After drying over magnesium sulfate and concentrating, the crude oil obtained is chromatographed over silica gel, and eluted with 3:2 hexane:ether to yield 3-bromophenol, n-pentyl ether as a clear oil.

At a temperature of −78° C., 19.4 ml of t-butyl lithium (1.7M) is added to 4.0 gm of the above 3-bromophenol, n-pentyl ether in 50 mls tetrahydrofuran; and to this is added 3.3 ml of a freshly prepared solution of $Li_2CuCl_3$ (0.10M/THF). The mixture is stirred for 10 minutes, and then 4.35 grams of the 1-bromo-5-benzyloxy pentane are added. The reaction is allowed to warm slowly to ambient temperature over 12 hours and is then stirred an additional 24 hours before being quenched with silica gel. After removing the solvent, the mixture is chromatographed over silica gel (1:1 hexane:ether) to yield a crude mixture containing 3-(benzyloxypentyl)-phenol, n-pentyl ether. A solution of 6.0 gm of this crude mixture in ethanol is hydrogenated over 5% Pd on carbon for 5 hours. After filtering through celite and concentrating, pure 3-(5-hydroxypentyl)-phenol, n-pentyl ether is obtained as a clear oil by HPLC chromatography.

Step B. (R)-3-Carboxy-N,N,N-trimethyl-2-[[hydroxy{5-[3-(pentyloxy)phenyl]pentyloxy}phosphinyl]oxy]-1-propanaminium Hydroxide, Inner Salt When the procedure of example 1 is carried out using an equivalent amount of the 3-(5-hydroxypentyl)-phenol, n-pentyl ether of Step A in place of the tetradecanol, the title compound is obtained (m.p. ~188° C. [dec.]; $^{31}P$ NMR=0.283 ppm).

EXAMPLE 16

(R)-3-Carboxy-N,N,N-trimethyl-2-[{hydroxy[5-(3-hexylphenyl)pentyloxy]phosphinyl}oxy]-1-propanaminium Hydroxide, Inner Salt Step A. 5-(3-hexylphenyl)-pentanol To 14.7 gm of the Wittig salt prepared from 1-bromopentane and triphenylphosphine in 80 ml of tetrahydrofuran at 0° C. is added 22.5 ml of n-butyl lithium (1.6M) in hexane. The mixture is stirred for 15 minutes, and 3.8 ml of 3-bromobenzaldehyde is added. This mixture is stirred for 30 minutes; and after concentrating and diluting with ether, the solids are filtered off. Further concentration of the filtrate and chromatography over silica gel eluting with 3:2 hexane:ether yields pure 3-bromo-(1-hexenyl)benzene as a clear oil.

At −78° C., 27.8 ml of t-butyl lithium (1.7M) in hexane are added to 5.30 gm of 3-bromo-(1-hexenyl)benzene in 75 mls of tetrahydrofuran. The reaction is stirred for 10 minutes, and then 1.1 ml of $Li_2CuCl_3$ (0.20M/THF) is added followed dropwise by 5.78 grams of 1-bromo-5-benzyloxy pentane. After allowing the reaction mixture to come to ambient temperature over 5 hours and stirring for an additional 24 hours, silica gel is added; and the mixture is concentrated and then chromatographed (HPLC) to yield pure 3-(5-benzyloxypentyl)-1-(1-hexenyl)benzene.

A solution of 840 mgs of 3-(5-benzyloxypentyl)(1-hexenyl)benzene in 25 mls of methanol is hydrogenated over 5% palladium on carbon and then filtered through celite, concentrated, and chromatographed over silica gel (3:2 ether:hexane) to yield pure 5-(3-hexylphenyl)-pentanol.

Step B. (R)-3-Carboxy-N,N,N-trimethyl-2-[{hydroxy[5-(3-hexylphenyl)pentyl]phosphinyl}oxy]-1-propanaminium Hydroxide, Inner Salt When the procedure of example 1 is carried out using an equivalent amount of the 5-(3-hexylphenyl)-pentanol of Step A in place of the tetradecanol, the title compound is obtained (m.p. >179° C.; $^{31}P$ NMR=0.353 ppm).

EXAMPLE 17

(R)-3-Carboxy-N,N,N-trimethyl-2-[[hydroxy{5-[4-(4-chlorophenoxy)-2-butyloxy}pentyloxy]phosphinyl]oxy]-1-propanaminium, Hydroxide, Inner Salt To a solution of 10.0 gms of p-chlorophenol in 60 ml of DMF are added 11.5 gms of $K_2CO_3$ followed by 7.03 gms of 1-bromo-3-butene, and this reaction mixture is stirred at room temperature for 18 hours. This mixture is then partitioned between ethyl acetate and water; and after separating, the organic layer is washed with brine, dried over $Na_2SO_4$, filtered, and concentrated under vacuum to give a brown liquid. This liquid is flash chromatographed with a 4/1 ratio of hexane and ethyl acetate to yield p-chlorophenyl-3-butenyl ether.

A mixture formed by adding 2.4 gms of 1,5-pentanediol and 2.1 gms of p-chlorophenyl-3-butenyl ether to a solution of 7.34 gms of mercuric acetate in 50 ml of DMF, is stirred at room temperature for 18 hours and following the addition of 25 ml of an aqueous NaOH solution (3 Molar), 25 ml of an aqueous $NaBH_4$ solution (0.5 Molar in 3 Molar NaOH) is added. The reaction is allowed to proceed for several minutes; and, after decanting the solution from the mercuric salts and concentrating, the residue is partitioned between ethyl acetate and water. The organic layer is separated, washed with brine, dried over $Na_2SO_4$, filtered, and concentrated again under vacuum. The residue is then flash chromatographed with a 10/1 ratio of hexane and ethyl acetate to yield 1-methyl-3-(p-chlorophenoxy)propyl-5-hydroxypentylether.

Following the procedure of Example 1 and using an equivalent amount of 1-methyl-3-(p-chlorophenoxy)propyl-5-hydroxypentylether in place of the tetradecanol, there is obtained (R)-3-Carboxy-N,N,N-trimethyl-2-[[hydroxy{5-[4-(4-chlorophenoxy)-2-butyloxy]pentyloxy}phosphinyl]oxy]-1-propanaminium hydroxide, inner salt (m.p. ~185° C. [dec.]; $^{31}P$ NMR=0.177 ppm).

EXAMPLE 18

(R)3-Carboxy-N,N,N-trimethyl-2-[{hydroxy[8-(2-aminophenoxy)octyloxy]phosphinyl}oxy]-1-propanaminium, Hydroxide, Inner Salt A solution of 490 mg of compound 56 from Example 5 in 5 ml of water and 490 mg of 10% Pd on carbon are flushed in a suitable flask with $H_2$ gas and stirred under an $H_2$-containing balloon for 2 days. The reaction mixture is added to a column of LiChroprep RP-8 silica gel and eluted sequentially with water, acetonitrile, and methanol. The product eluted in the methanol is evaporated to yield (R)-3-Carboxy-N,N,N-trimethyl-2-[{hydroxy[8-(2-aminophenoxy)octyloxy]phosphinyl}oxy]-1-propanaminium hydroxide, inner salt $^{31}P$ NMR=0.381 ppm; $[\alpha]^{25} = -10.07$ C=1.0 MeOH)).

When the above procedure is carried out using an equivalent amount of compound 44 from Example 5 in place of compound 57, there is obtained (R)-3-Carboxy-N,N,N-trimethyl-2-[{hydroxy[8-(4-aminophenoxy)octyloxy]phosphinyl}oxy]-1-propanaminium hydroxide, inner salt ($^{31}P$ NMR=0.383 ppm).

EXAMPLE 19

(R)-3-Carboxy-N,N,N-trimethyl-2-[[hydroxy{4-[3-(4-triflouromethoxyphenoxy)phenoxy]butoxy}phosphinyl]oxy]-1-propanaminium Hydroxide, Inner Salt Step A. 4-(3-Bromophenoxy)butan-1-ol To a solution of 7.0 g of 3-bromophenol and 7.8 g of ethyl 4-bromobutyrate in 50 ml of DMF is added 11.2 g of K₂CO₃. The mixture is heated at 60° C. for 1 day and then poured into an ice-water mixture. This mixture is extracted with ether, and the ether extract is washed with water and dried over MgSO₄. After filtration and concentration, a solution of 9.3 g of the ethyl 4-(3-bromophenoxy)butyrate obtained in 100 ml of THF is cooled to 0° C.; and 130 ml of a 1.5M solution of DIBAL-H in toluene is added dropwise. The reaction is stirred for 1 hour at 0° C. and 2 hours at room temperature, following which the reaction mixture is poured into a mixture of ice/3N HCl and extracted with ether. The ether extract is washed with water and dried over MgSO₄. Filtration and concentration yields 4-(3-Bromophenoxy)butan-1-ol.

Step B. 4-{3-[4-(Trifluoromethoxy)phenoxy]phenoxy}butan-1-ol

In a suitable flask, 3.9 g of 4-(trifluoromethoxy)-phenol, 5.2 g of 4-(3-bromophenoxy)butan-1-ol, and 5 g of K₂CO₃ are flushed with N₂ gas, and 25 ml of pyridine are added. The reaction is heated to 90° C. and 4.2 g of CuO are added. The reaction mixture is then heated at reflux for 24 hours. After cooling, the mixture is filtered, concentrated, and dissolved in ether. The ether solution is washed with dilute HCl, then twice with water, and then dried over MgSO₄. After filtration and concentration, the crude product is purified by flash chromatography on silica gel with 20% EtOAc/hexane as eluant to yield 4-{3-[4-(trifluoromethoxy)phenoxy]-phenoxy}butan-1-ol.

Step C. (R)-3-Carboxy-N,N,N-trimethyl-2-[[hydroxy{4-[3-(4-triflouromethoxyphenoxy)phenoxy]butoxy}phosphinyl]oxy]-1-propanaminium Hydroxide, Inner Salt When the procedure of example 1 is carried out using an equivalent amount of the 4-{3-[4-(trifluoromethoxy)-phenoxy]phenoxy}butan-1-ol of step B of this example in place of the tetradecanol, there is obtained (R)-3-Carboxy-N,N,N-trimethyl-2-[[hydroxy{4-[3-(4-triflouromethoxyphenoxy)phenoxy]butoxy}phosphinyl]oxy]-1-propanaminium hydroxide, inner salt (m.p. 184°-6° C. [dec.]; ³¹P NMR=0.286 ppm; [α]²⁵ = −7.51 C=1.0 MeOH)).

EXAMPLE 20

81)
(R)-3-Carboxy-N,N,N-trimethyl-2-[[hydroxy{4-[4-(4-triflouromethoxyphenoxy)phenoxy]butoxy}phosphinyl]oxy]-1-propanaminium Hydroxide, Inner Salt Step A. 4-(4-Hydroxyphenoxy)butan-1-ol To a solution of 16.52 g of p-hydroquinone and 9.75 g of ethyl 4-bromobutyrate in 150 ml of DMF are added 10.37 g of K₂CO₃, and this mixture is stirred at room temperature for 3 days and then filtered. After removal of most of the DMF by rotary evaporation, the residue is partitioned between EtOAc and dilute HCl. The water phase is separated and extracted further with 2 portions of EtOAc. The combined EtOAc layers are washed with water, then brine, and then dried over MgSO₄. After filtration and evaporation, an oily residue is obtained, which is purified by flash chromatography on silica gel with 4:1 hexane/EtOAc followed by 3:1 hexane/EtOAc as eluant to yield 4-(4-Hydroxyphenoxy)butyrate.

A solution of 5.07 g of ethyl 4-(4-hydroxyphenoxy)-butyrate in 23 ml of ether is added dropwise to a mixture of 1.72 g of lithium aluminum hydride in 90 ml of ether at a rate which maintains a gentle reflux. The mixture is stirred at ambient temperature for 6 hours, and then water is carefully added followed by 3N HCl to dissolve all solids. After separating the ether phase and extracting the aqueous phase twice with ether, the combined ether phases are washed with saturated NaHCO₃, water, and brine and dried over MgSO₄. Filtration and concentration yields 4-(4-hydroxyphenoxy)butan-1-ol as a white solid.

Step B. 4-[4-(4-Trifluoromethoxyphenoxy)phenoxy]butan-1-ol

A mixture of 3.13 g of 4-(4-hydroxyphenoxy)butan-1-ol, 4.97 g of 4-(trifluoromethoxy)bromobenzene, and 4.75 g of K₂CO₃ are placed in a flask and flushed with N₂ gas. To this are added 17 ml of pyridine and, after heating to 90° C., 3.42 g of CuO. The reaction mixture is heated at reflux for 2 days, and then cooled and poured into an ice/3N HCl mixture. This mixture is extracted twice with ether; and after separating, the combined ether extracts are washed with saturated NaHCO₃, followed by brine, and then dried over MgSO₄. Filtration and evaporation yields an oily residue which is purified by flash chromatography on silica gel, using 2:1 hexane/EtOAc as eluant. After evaporation, 4-[4-(4-(trifluoromethoxyphenoxy)phenoxy]butan-1-ol is obtained as a white solid.

Step C. (R)-3-Carboxy-N,N,N-trimethyl-2-[[hydroxy{4-[4-(4-triflouromethoxyphenoxy)phenoxy]butoxy}phosphinyl]oxy]-1-propanaminium Hydroxide, Inner Salt When the procedure of example 1 is carried out using an equivalent amount of the 4-{4-[4-(Trifluoromethoxy)phenoxy]phenoxy}butan-1-ol of step B of this example in place of the tetradecanol, there is obtained (R)-3-Carboxy-N,N,N-trimethyl-2-[[hydroxy{4-[4-(4-triflouromethoxyphenoxy)phenoxy]butoxy}phosphinyl]oxy]-1-propanaminium hydroxide, inner salt (³¹P NMR=0.078 ppm; [α]²⁵ = −7.54 C=1.0 MeOH)).

Following the procedure of this example but using an equivalent amount of resorcinol for the p-hydroquinone in Step A, and an equivalent amount of 2-bromonaphthalene for 4-(trifluoromethoxy)bromobenzene in Step B, there is obtained (R)-3-Carboxy-N,N,N-trimethyl-2-[[hydroxy{4-[3-(2-naphthoxy)phenoxy]butoxy}phosphinyl]oxy]-1-propanaminium hydroxide, inner salt (m.p. ~175° C. [dec.]; ³¹P NMR=0.060 ppm).

EXAMPLE 21

(R)-3-Carboxy-N,N,N-trimethyl-{[hydroxy(tetradecyloxy)phosphinyl]oxy}-1-propanaminium Hydroxide, Inner Salt A 5-liter, 4-necked round-bottomed flask, equipped with a mechanical stirrer, thermometer, addition funnel, drying tube and cooling bath is charged with 153 ml of phosphorus trichloride and 625 ml of heptane; and 125 g of 1-tetradecanol dissolved in 625 ml of heptane are added over a period of 50-55 minutes while maintaining an internal temperature of 23°-25° C. This mixture is stirred for 45 minutes and then concentrated at 40°-45° C. under a reduced pressure of 25-30 mm Hg until 1.2 liters of solvent is removed. The resulting crude oil is dissolved in 1.25 liters of tetrahydrofuran; and 75.5 g of L-carnitine are added while maintaining an internal temperature of 25°-30° C. The suspension formed is stirred for 5 minutes, and a solution of 231 ml of 2,4,6-collidine in 1.25 liters of tetrahydrofuran is added over a period of 40 minutes while maintaining an internal temperature of 25°-30° C. The resulting white slurry is cooled to 22°-23° C. and stirring is continued for 3 hours. The mixture is cooled to 0°-5° C., and 750 ml of deionized plant water are added over a period of 10 minutes while maintaining an internal temperature of 5°-10° C. A total of 125 g of sodium periodate are then added in three equal 41.7 g portions over a period of 30 minutes at 10 minute intervals, while maintaining an internal temperature of 10°-15° C. The reactants are warmed to 22°-23° C. and stirred an additional 1.5 hour. The mixture is then cooled to 0°-5° C., and 250 g of sodium thiosulfate dissolved in 500 mL of deionized plant water are added over a period of 30 minutes while maintaining an internal temperature of 5°-10° C. The reaction mixture is warmed to 22°-23° C. and stirred for 30 minutes. After separating the solids by suction filtration, the filtrate is concentrated under reduced pressure (100 mbar) at 45°-50° C., until 2.25 liters of solvent is collected. The crude mixture obtained is transferred to a 5-liter, 4-necked round-bottomed flask, equipped with a mechanical stirrer, thermometer, addition funnel, and cooling bath and is diluted with 45 g of sodium carbonate dissolved in 350 mL of deionized plant water over a period of 20 minutes while maintaining an internal temperature of 22°-23° C. After addition is complete, 2.0 liters of ethyl acetate are added, and the two-phase mixture is stirred for 30 minutes while maintaining an internal temperature of 22°-23° C. The layers are separated, and the organic phase is discarded. The aqueous layer is cooled to 0°-5° C. and 120 mL of concentrated hydrochloric acid are added over a period of 30 minutes while maintaining an internal temperature of 5°-10° C. The resulting solution is warmed to 22°-23° C. to yield 2.3 liters of an aqueous solution of crude 3-carboxy-2(R)-N,N,N-trimethyl-{[hydroxy(tetradecyloxy)phosphinyl]oxy}-1-propanaminium hydroxide, inner salt.

To the crude product are added 400 g of reverse phase silica gel (C-8), and the resulting slurry is stirred for 45 minutes. The resulting gel is collected by filtration over a 3-liter glass fritted funnel using suction. This treatment is repeated twice with 400 g portions and then with a 200 g portion of silica gel. The gel fractions are mixed together and then eluted with HPLC grade water using suction until the conductance of the filtrate reaches <100 μS/cm. This is followed by 7.5 liters of absolute ethanol. The first 0.82 liters of solvent, collected after switching to elution with ethanol, is discarded. The next 5.9 liters of solvent collected are concentrated under reduced pressure (25-30 mm Hg) at 40°-45° C. until 5.5 liters of solvent are collected. The resulting thick slurry is transferred, with the aid of sufficient absolute ethanol (approximately 400 ml) to bring the volume to 1 liter, to a 5-liter, 4-necked, round-bottomed flask, equipped with a mechanical stirrer, thermometer, addition funnel and heating mantle and warmed to 55°-60° C. To the solution obtained, 1.8 liters of THF are added over a period of 30 minutes while maintaining an internal temperature of 50°-55° C. After cooling to 22°-23° C. over 2 hours and stirring for an additional 1 hour, the solids are collected by filtration under suction and washed with three 100 ml portions of THF. The solid are transferred to a 2-liter, 4-necked, round-bottomed flask, and 475 ml of 95% ethanol are added. The suspension obtained is warmed to 50°-55° C., and the resulting solution is filtered under suction into a 5-liter, 4-necked, round bottomed flask, equipped with a heating mantle, thermometer, mechanical stirrer and addition funnel. This solution is warmed to 50°-55° C., and 1.25 liters of THF are added over a period of 30 minutes while maintaining an internal temperature of 50°-55° C. The mixture is cooled to 22°-23° C. over 2.0 hours and stirred for an additional 1.0 hour. The solids formed are collected by filtration under suction and washed with a total of 300 ml of THF in three equal portions of 100 ml each followed by 150 ml of acetone. The solids are then dried at 45°-50° C. at 25-30 mm Hg for about 16 hours until the weight is constant to obtain 110 g of pure 3-Carboxy-2(R)-{[hydroxy(tetradecyloxy)phosphinyl]oxy}-N,N,N-trimethyl-1-propanaminium hydroxide, inner salt (yield 54%).

Alternatively, the above purification can be carried out using AMBERLITE XAD-4 nonionic polymeric adsorbent in place of the expensive reverse phase silica gel (C-8) by treating 1.5 kg of AMBERLITE XAD-4 with the crude product solution above in the same manner as described for the reverse phase silica gel (C-8). By eluting with water followed by 7.5 liters of absolute ethanol, 5.9 liters of solution containing the desired product is obtained. Evaporation of 5.5 liters of ethanol from the resulting solution results in a slurry, which is dissolved in an additional 400 ml of ethanol by heating to 55°-60° C. to yield 1 liter of solution. The pure title compound is crystallized from the solution by adding 1.8 liters of THF and drying.

What is claimed is:

1. A process for preparing a compound of the formula:

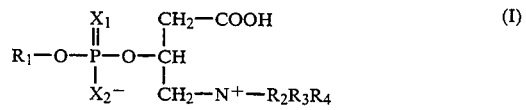

where $X_1$ and $X_2$ are independently O or S, and
$R_1$ is $R_5$—Y—$R_6$ or $R_7$—Z—$R_8$,
where
Y is —O—, —S—, —$CH_2$—, —CH=CH—, —C≡C—, —N($R_{10}$)—CO—, or —CO—N($R_{10}$)—,
Z is —O—, —S— or —$CH_2$—,
$R_5$ is straight or branched chain ($C_{1-17}$)alkyl or ω-triflouro-($C_{1-8}$)alkyl, and
$R_6$ is straight chained ($C_{2-18}$)alkylene,
and the total number of carbons in $R_5$—Y—$R_6$ is from 7 to 19,
$R_7$ is unsubstituted phenyl, phenoxyphenyl, biphenyl, naphthyl or naphthoxyphenyl, or phenyl, phenoxyphenyl, biphenyl, naphthyl or naphthoxyphenyl mono-, di-, or tri-substituted with halogen, $NO_2$, $NH_2$, CN, ($C_{1-8}$)alkyl, ($C_{1-8}$)alkoxy, triflouromethyl, triflouromethoxy, or acetyl,
$R_8$ is straight chained ($C_{3-15}$)alkylene, —($CH_2$)$_m$—N($R_{10}$)—CO—($CH_2$)$_n$—, —($CH_2$)$_m$—CO—N($R_{10}$)—($CH_2$)$_n$—, or —$CH_2$—$R_{11}$—O—$R_{12}$—,
m is 1 to 7,
n is 1 to 7,
$R_{10}$ is hydrogen, methyl, or ethyl,
$R_{11}$ is straight or branched chain alkyl of 1 to 7 carbon atoms,
$R_{12}$ is straight chained ($C_{2-7}$)alkylene,
and the total number of carbons in the aryl substituents of $R_7$ and the carbon atoms in $R_8$ is from 3 to 15, $R_2$, $R_3$, and $R_4$ are each independently straight or branched chain $(C_{1-4})$alkyl, and pharmaceutically acceptable salts, physiological hydrolysable esters, and pro-drug forms thereof, comprising the steps of A) reacting a compound of the formula $$R_1-O-P-Q_2 \quad (II)$$

with a compound of the formula $$\begin{array}{c} CH_2-COO^- \\ | \\ HO-CH \\ | \\ CH_2-N^+R_2R_3R_4 \end{array} \quad (III)$$

in an inert solvent;

Bi) oxidizing and hydrolysing the product obtained with an oxidizing agent of the formula $$NaQ'O_4$$

where $R_1$, $R_2$, $R_3$, and $R_4$ are as defined above and Q and Q' are independently chlorine, bromine, or iodine, in water to obtain a compound of formula (I) in which $X_1$ and $X_2$ are oxygen, or Bii) thiolating and hydrolysing the product obtained in step A with sulfur and water to obtain a compound of formula (I) in which one of $X_1$ and $X_2$ is sulfur and the other is oxygen, or Biii) sulfating and sulfolysing the product obtained in step A with sulfur and hydrogen sulfide to obtain a compound of formula (I) in which both $X_1$ and $X_2$ are sulfur; and C) isolating and purifying the compound of formula (I) by chromatography over reverse phase silica gel (C-8) or AMBERLITE XAD-4 nonionic polymeric adsorbent.

2. A process according to claim 1 comprising the steps of:

A) reacting a compound of the formula $$R_1-O-P-Q_2 \quad (II)$$

with a compound of the formula $$\begin{array}{c} CH_2-COO^- \\ | \\ HO-CH \\ | \\ CH_2-N^+R_2R_3R_4 \end{array} \quad (III)$$

in an inert solvent;

Bi) oxidizing and hydrolysing the product obtained with an oxidizing agent of the formula $$NaQ'O_4$$

in water to obtain a compound of formula (I) in which $X_1$ and $X_2$ are oxygen; and C) isolating and purifying the compound of formula (I) by chromatography over reverse phase silica gel (C-8) or AMBERLITE XAD-4 nonionic polymeric adsorbent, where $R_1$, $R_2$, $R_3$, $R_4$, Q, and Q' are as defined above.

3. A process according to claim 1 comprising the steps of:

A) reacting a compound of the formula $$R_1-O-P-Q_2 \quad (II)$$

with a compound of the formula $$\begin{array}{c} CH_2-COO^- \\ | \\ HO-CH \\ | \\ CH_2-N^+R_2R_3R_4 \end{array} \quad (III)$$

in an inert solvent;

Bii) thiolating and hydrolysing the product obtained with sulfur and water to obtain a compound of formula (I) in which one of $X_1$ and $X_2$ is sulfur and the other is oxygen; and C) isolating and purifying the compound of formula (I) by chromatography over reverse phase silica gel (C-8) or AMBERLITE XAD-4 nonionic polymeric adsorbent, where $R_1$, $R_2$, $R_3$, $R_4$, Q, and Q' are as defined above.

4. A process according to claim 1 comprising the steps of:

A) reacting a compound of the formula $$R_1-O-P-Q_2 \quad (II)$$

with a compound of the formula $$\begin{array}{c} CH_2-COO^- \\ | \\ HO-CH \\ | \\ CH_2-N^+R_2R_3R_4 \end{array} \quad (III)$$

in an inert solvent;

Biii) sulfating and sulfolysing the product obtained with sulfur and hydrogen sulfide to obtain a compound of formula (I) in which both $X_1$ and $X_2$ are sulfur; and C) isolating and purifying the compound of formula (I) by chromatography over reverse phase silica gel (C-8) or AMBERLITE XAD-4 nonionic polymeric adsorbent, where $R_1$, $R_2$, $R_3$, $R_4$, Q, and Q' are as defined above.

5. A process according to claim 1 in which the compound 1 of formula (I) is:

$$\begin{array}{c} \phantom{R_1-O-}X_1 \phantom{-O-}CH_2-COOH \\ \phantom{R_1-O-}\| \phantom{-O-}| \\ R_1-O-P-O-CH \\ \phantom{R_1-O-}| \phantom{-O-}| \\ \phantom{R_1-O-}X_2^- \phantom{-O-}CH_2-N^+-R_2R_3R_4 \end{array} \quad (I)$$

where $X_1$ and $X_2$ are independently an oxygen or sulfur atom, $R_1$ is $R_5-Y-R_6$ or $R_7-Z-R_8$, where Y is $-O-$, $-S-$, $-CH_2-$, $-CH=CH-$, or $-C\equiv C-$, Z is $-O-$, or $-S-$, $R_5$ is straight or branched chain $(C_{1-17})$alkyl, and $R_6$ is straight chained $(C_{2-18})$alkylene, and the total number of carbons in $R_5$ and $R_6$ is from 7 to 19, $R_7$ is unsubstituted phenyl, biphenyl, or naphthyl or phenyl or naphthyl mono-, di-, or tri-substituted with halogen, $NO_2$, $(C_{1-8})$alkyl, $(C_{1-8})$alkoxy, triflouromethyl, triflouromethoxy, or acetyl, and $R_8$ is straight chained $(C_{3-15})$alkylene,
and the total number of carbons in the substituents in $R_7$ and in $R_8$ is from 3 to 15, $R_2$, $R_3$, and $R_4$ are each independently straight or branched chain $(C_{1-4})$alkyl, or a pharmaceutically acceptable salt or a pysiologically hydrolyable ester or a pro-drug form thereof.

6. A process according to claim 2 in which $X_1$ and $X_2$ are both oxygen and $R_1$ is $R_5$—$CH_2$—$R_6$.

7. A process according to claim 2 in which the compound 1 of formula (I) is (R)-3-Carboxy-N,N,N-trimethyl-2-{[hydroxy(tetradecyloxy)phosphinyl]oxy}-1-propanaminium, hydroxide, inner salt.

8. A process according to claim 2 in which the compound of formula (I) is (R)-3-Carboxy-N,N,N-trimethyl-2-[[hydroxy{4-[3-(hexyloxy)phenoxy]butyloxy}phosphinyl]oxy]-1-propanaminium, hydroxide, inner salt.

* * * * *